United States Patent
Weitzman

(10) Patent No.: US 9,204,891 B2
(45) Date of Patent: Dec. 8, 2015

(54) FLEXIBLE SURGICAL DEVICE FOR TISSUE REMOVAL

(75) Inventor: Yoseph Weitzman, Tel-Aviv (IL)

(73) Assignee: Carevature Medical Ltd., Tel-Aviv (IL)

( * ) Notice: Subject to any disclaimer, the term of this patent is extended or adjusted under 35 U.S.C. 154(b) by 137 days.

(21) Appl. No.: 13/808,643

(22) PCT Filed: Jul. 7, 2011

(86) PCT No.: PCT/IB2011/053035
§ 371 (c)(1),
(2), (4) Date: Jan. 7, 2013

(87) PCT Pub. No.: WO2012/004766
PCT Pub. Date: Jan. 12, 2012

(65) Prior Publication Data
US 2013/0110145 A1    May 2, 2013

Related U.S. Application Data

(60) Provisional application No. 61/361,930, filed on Jul. 7, 2010.

(51) Int. Cl.
*A61B 17/32* (2006.01)
*A61B 17/3205* (2006.01)
*A61B 17/16* (2006.01)
*A61B 17/17* (2006.01)
*A61B 17/29* (2006.01)

(52) U.S. Cl.
CPC ......... *A61B 17/3205* (2013.01); *A61B 17/1642* (2013.01); *A61B 17/1671* (2013.01); *A61B 17/1757* (2013.01); *A61B 2017/2927* (2013.01)

(58) Field of Classification Search
CPC ............... A61B 17/16; A61B 17/1642; A61B 17/1671; A61B 17/3205; A61B 17/320758; A61B 17/1757; A61B 2017/2927
USPC ................... 606/79, 80, 84, 85, 170
See application file for complete search history.

(56) References Cited

U.S. PATENT DOCUMENTS

| 5,527,316 | A  | 6/1996 | Stone et al. |
| 6,558,390 | B2 | 5/2003 | Cragg |
| 7,014,633 | B2 | 3/2006 | Cragg |
| 7,189,240 | B1 | 3/2007 | Dekel |
| 7,585,300 | B2 | 9/2009 | Cha |
| D606,654  | S  | 12/2009 | Tran et al. |

(Continued)

FOREIGN PATENT DOCUMENTS

| DE | 10360076 | 4/2005 |
| NL | 1009471 | 12/1999 |
| WO | WO 2012/004766 | 1/2012 |

OTHER PUBLICATIONS

International Preliminary Report on Patentability Dated Jan. 17, 2013 From the International Bureau of WIPO Re. Application No. PCT/IB2011/053035.

(Continued)

*Primary Examiner* — Ashley Fishback

(57) ABSTRACT

An elongate tool with a cutting end. In some embodiments the end is bendable. Optionally, the end is bendable between two cutting edges. Optionally or alternatively, the end includes both a forward cutting edge and a side cutting edge. The tool may be sized for hand-held use, with control from outside the body, for treating a spinal stenosis.

30 Claims, 26 Drawing Sheets

(56) References Cited

U.S. PATENT DOCUMENTS

| | | |
|---|---|---|
| D611,146 S | 3/2010 | Way et al. |
| 8,221,424 B2 | 7/2012 | Cha |
| 2006/0089609 A1 | 4/2006 | Bleich et al. |
| 2006/0135882 A1 | 6/2006 | Bleich |
| 2006/0200155 A1 | 9/2006 | Harp |
| 2006/0241648 A1 | 10/2006 | Bleich et al. |
| 2008/0004645 A1 * | 1/2008 | To et al. .................. 606/159 |
| 2008/0086034 A1 | 4/2008 | Schmitz et al. |
| 2008/0183175 A1 | 7/2008 | Saal et al. |
| 2008/0183192 A1 | 7/2008 | Saal et al. |
| 2008/0221605 A1 | 9/2008 | Saal et al. |
| 2009/0036936 A1 | 2/2009 | Solsberg et al. |
| 2009/0143807 A1 | 6/2009 | Sand |
| 2010/0042104 A1 | 2/2010 | Kota et al. |
| 2010/0082033 A1 | 4/2010 | Germain |
| 2010/0211076 A1 | 8/2010 | Germain et al. |
| 2010/0262147 A1 | 10/2010 | Siegal et al. |
| 2010/0286695 A1 | 11/2010 | Hannani et al. |
| 2010/0298832 A1 | 11/2010 | Lau et al. |

OTHER PUBLICATIONS

Communication Relating to the Results of the Partial International Search Dated Dec. 6, 2011 From the International Searching Authority Re. Application No. PCT/IB2011/053035.

International Search Report and the Written Opinion Dated Feb. 9, 2012 From the International Searching Authority Re. Application No. PCT/IB2011/053035.

Official Action Dated Apr. 14, 2015 From the US Patent and Trademark Office Re. U.S. Appl. No. 13/808,643.

* cited by examiner

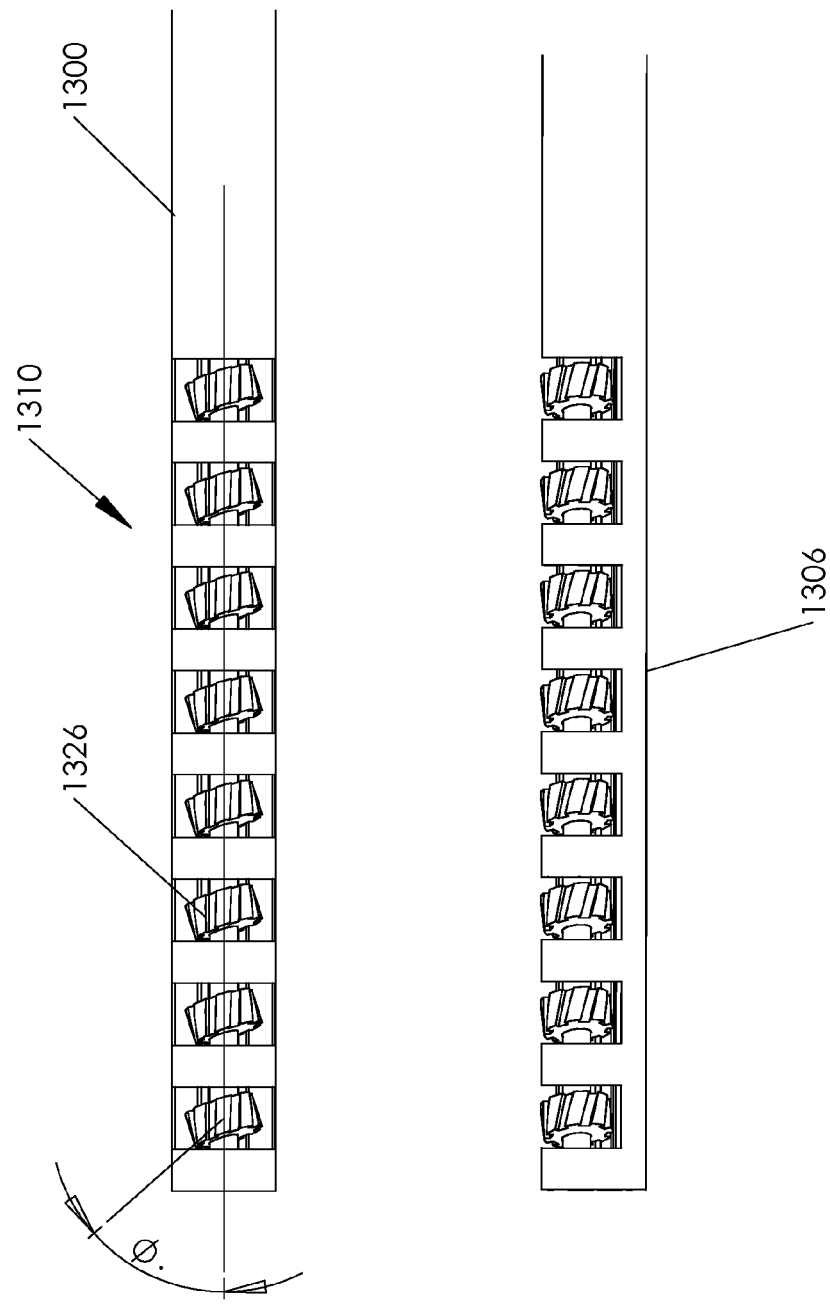

FLEXIBLE SURGICAL DEVICE FOR TISSUE REMOVAL

RELATED APPLICATIONS

This application is a National Phase of PCT Patent Application No. PCT/IB2011/053035 having International filing date of Jul. 7, 2011, which claims the benefit of priority under 35 USC §119(e) of U.S. Provisional Patent Application No. 61/361,930 filed on Jul. 7, 2010. The contents of the above applications are all incorporated by reference as if fully set forth herein in their entirety.

FIELD AND BACKGROUND OF THE INVENTION

The present invention, in some embodiments thereof, relates to surgical devices and, more particularly, but not exclusively, to a method and apparatus for removing tissue from body organs.

Minimally-invasive surgery generally involves use of endoscopic or similar devices which may be inserted through incisions in the skin, through body cavities, and/or through other anatomical openings. The procedures frequently involve remote-control manipulation of instruments for removing tissue from body organs, such as in the circulatory system, digestive system, nervous system, muscular system, skeletal system, and the other systems of the body. Occasionally, the tissues are difficult to access or may be positioned close to organs which are delicate and relatively easily damaged. This may require that additional incisions be made in the body for accessing the area and/or for introducing additional surgical instruments and/or facilitating operation of the instruments.

Spinal stenosis is an example of a condition where tissue removal is made relatively difficult due to the difficulty in accessing the spinal canal (neuroforamen) and the proximity to the spinal cord. Devices and methods have been suggested in the art which attempt to treat conditions such as those of spinal stenosis using minimally-invasive surgery.

U.S. Patent Publication US 2006/0200155 to Harp describes "a reciprocating surgical file system for precisely removing bone and/or other tissue. The system allows a user to maneuver the system and navigate into hard-to-access sites under a direct vision mechanism. A transmission mechanism converts rotary motion from a motor into reciprocating motion and provides it to the surgical file for precision removal of bone or other tissue. A pulsatile pump mechanism is operatively coupled with the transmission mechanism and provides irrigating fluid to the surgical site."

U.S. Patent Publication US 2006/0135882 to Bleich describes "methods and apparatus are provided for selective surgical removal of tissue. In one variation, tissue may be ablated, resected, removed, or otherwise remodeled by standard small endoscopic tools delivered into the epidural space through an epidural needle. The sharp tip of the needle in the epidural space, can be converted to a blunt tipped instrument for further safe advancement. The current invention includes specific tools that enable safe tissue modification in the epidural space, including a barrier that separates the area where tissue modification will take place from adjacent vulnerable neural and vascular structures. A nerve stimulator may be provided to reduce a risk of inadvertent neural abrasion."

U.S. Pat. No. 7,189,240 to Dekel describes "a method of treating spinal stenosis, in which a rasp is brought through a part of a spinal channel and then axially moved so that the rasp removes a stenosis in the spinal channel. Optionally, a shield protects a spinal cord or other sensitive tissues in the spinal channel."

Additional background art includes U.S. Patent Publications 2006/0089609, 2006/0241648, 2008/0086034, 2009/0036936, 2009/0143807, 2010/0262147, 2008/0183175, 2008/0183192, 2008/0221605, 2010/0082033, 2010/0211076, 2006/0200155, 2010/0286695, 2010/0298832; U.S. Pat. Nos. 6,558,390, 7,014,633; U.S. Design Pat. D611146, D606654; Foreign Patent NL1009471.

SUMMARY OF THE INVENTION

There is provided in accordance with an exemplary embodiment of the invention, a surgical device for removing tissue from a body organ comprising an elongated shaft distally attached to a flexible cutting section having a plurality of cutting edges and at least one bending point between adjacent cutting edges.

In an exemplary embodiment of the invention, said distal section includes a shield for shielding tissue from said cutting edges. Optionally or alternatively, said shield is rotatable around and/or axially movable along a longitudinal axis of said cutting section. Optionally or alternatively, the device comprises a blade adjustment mechanism for adjusting a distance at least a portion of said cutting edges protrude transaxially from said cutting section. Optionally, said protruding distance varies along a length of the cutting section. Optionally or alternatively, said blade adjustment mechanism includes a rotary cam mechanism.

In an exemplary embodiment of the invention, said cutting section is bendable during cutting In an exemplary embodiment of the invention, said cutting section cuts a concave shape along a longitudinal axis of the section.

In an exemplary embodiment of the invention, said cutting section is axially bendable along an angle ranging from −270 degrees to 270 degrees in a single plane.

In an exemplary embodiment of the invention, said cutting section is axially bendable along an angle ranging from −270 degrees to 270 degrees in three dimensional space.

In an exemplary embodiment of the invention, said plurality of cutting edges form part of a continuous spiral cutting edge.

In an exemplary embodiment of the invention, said plurality of cutting edges are composed of a plurality of separate cutting discs.

In an exemplary embodiment of the invention, said cutting section is rotatable around a longitudinal axis of said elongated shaft.

In an exemplary embodiment of the invention, the device includes a movement mechanism for bending said cutting section. Optionally, said movement mechanism includes at least one pull wire. Optionally or alternatively, said pull wire is positioned so that it lays off-axis relative to a natural bending axis of said cutting section.

In an exemplary embodiment of the invention, said cutting section is adapted to cut tissue laterally.

In an exemplary embodiment of the invention, said cutting section includes a distal tip. Optionally, said distal includes a frontal cutting tool.

In an exemplary embodiment of the invention, said surgical device is disposable.

In an exemplary embodiment of the invention, said device is handheld.

In an exemplary embodiment of the invention, said bending point is a predefined joint.

In an exemplary embodiment of the invention, said bending point is a point along a continuously bendable cutting element.

Optionally a surgical device according to any of the preceding claims, wherein said cutting section is bendable relative to said shaft such that their longitudinal axes are at least at an angle less than 150 degrees relative to one another.

There is provided in accordance with an exemplary embodiment of the invention, a surgical device for removing tissue material from under a tissue surface comprising an elongated shaft and a distally attached tip including a cutting tool, said distal tip attached to said shaft such that their longitudinal axes are at least at an angle less than 150 degrees relative to one another. Optionally, said angle is less than 90 degrees. Optionally or alternatively, said angle is less than 60 degrees. Optionally or alternatively, said device bends at point between two cutting edges.

There is provided in accordance with an exemplary embodiment of the invention, a method for removing tissue from a body organ comprising:
  forward cutting tissue from said organ;
    advancing said forward cutting based on determining an amount of tissue removed by forward cutting;
  simultaneously forward cutting and laterally cutting tissue; and
  advancing said forward and lateral cutting based on determining an amount of tissue removed by said forward and lateral cutting. Optionally, said advancing is based on feedback. Optionally or alternatively, the method comprises changing a bending angle and/or a bending point of a tool used for said cutting, for said advancing. Optionally, the method comprises inserting a cutting tool via a small opening and then at least laterally expanding said tool. Optionally, said expanding is controlled from outside the body.

In an exemplary embodiment of the invention, the method comprises cutting by rotating.

In an exemplary embodiment of the invention, said tissue removal forms an indirect passage. Optionally or alternatively, said tissue removal is between a ligament and a spinal bone. Optionally or alternatively, the method comprises cutting while a cutting section of a cutting tool is bent. Optionally or alternatively, the method comprises controlling cutting parameters from outside the body.

There is provided in accordance with an exemplary embodiment of the invention, a surgical device for removing tissue from a body organ comprising an elongated shaft and a distally attached cutting section including at least one cutting edge for lateral cutting and a frontal cutting edge for forward cutting. Optionally, said cutting edges are part of rotating cutting tools. Optionally or alternatively, said device is adapted to bend during operation of said edges, at a point between said edges. Optionally or alternatively, said device includes at least two conduits reaching to a distal side of said shaft.

There is provided in accordance with an exemplary embodiment of the invention, a surgical device kit for removing tissue from body organs comprising:
  an elongated shaft including a proximal handle; and
  a cutting section having a plurality of cutting edges;
    wherein said cutting section attaches to said elongated shaft and is adapted to bend relative to said shaft. Optionally, the kit comprises a handle. Optionally, said handle includes a power source and a motive source and a bending-actuator, for said cutting section.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 13 schematically illustrates an exemplary surgical probe including a cutting section having a rotary cutting blade with rotary cutting wheels forming an angle θ with a longitudinal axis of the probe, according to some embodiments of the present invention;

DESCRIPTION OF SPECIFIC EMBODIMENTS OF THE INVENTION

Figure 1A:
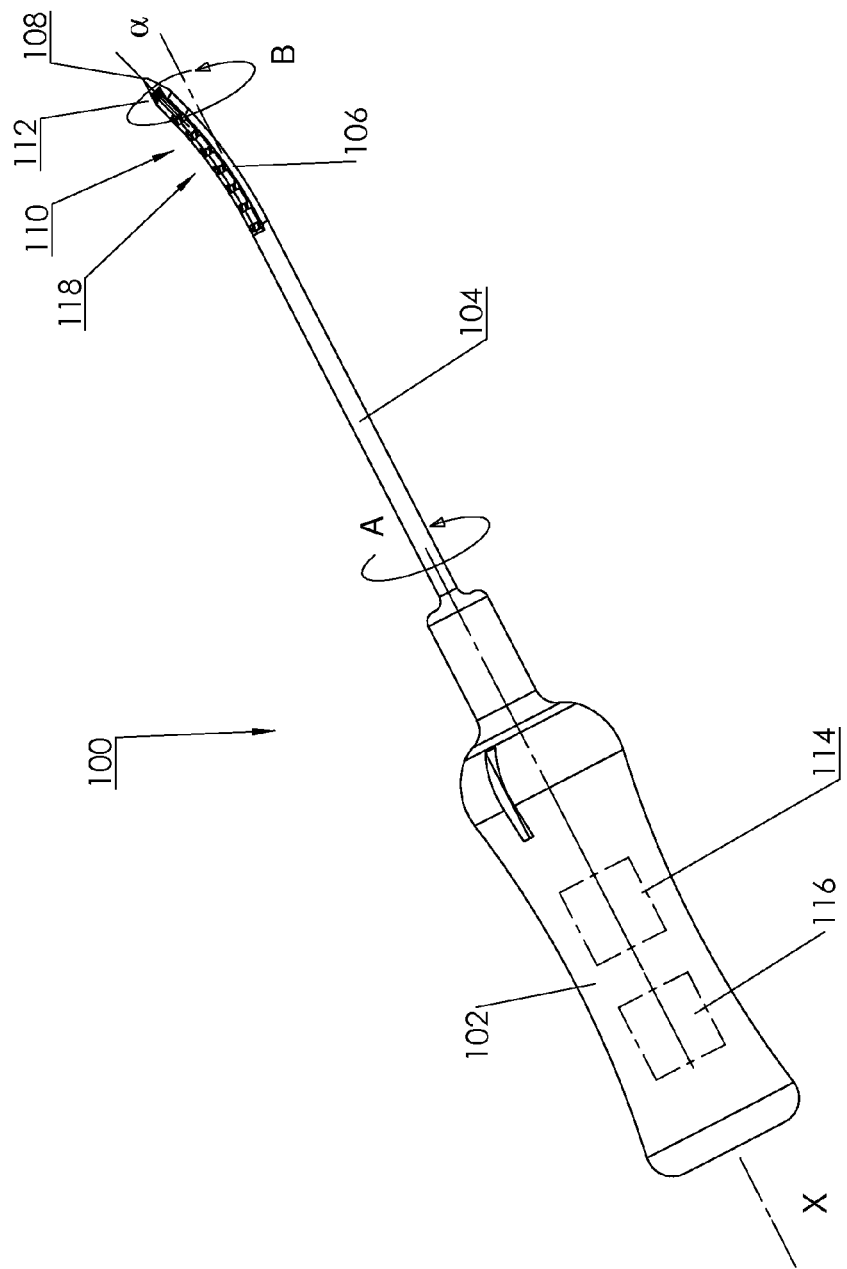
FIG. 1A schematically illustrates a perspective view of an exemplary surgical probe having a slightly flexed distal end, according to an embodiment of the present invention.

The present invention, in some embodiments thereof, relates to surgical devices and, more particularly, but not exclusively, to a method and apparatus for removing tissue from body organs.

An aspect of some embodiments of the present invention relates to a surgical probe including a cutting section with an optional shield and having a cutting blade for laterally cutting tissue from body organs. In an exemplary embodiment of the invention, the probe, which optionally includes a proximal control handle for manipulating the probe and a probe shaft including the cutting section, is adapted to be placed laterally against tissue and to selectively cut only tissue exposed to the cutting blade while shielding surrounding tissue from the blade. Optionally, a tissue cutting rate is greater than 1 mm3 per second for cortical bone, for example, 5 mm3/sec, 10 mm3/sec, 15 mm3/sec, 25 mm3/sec, or greater or intermediate values. Optionally, the cutting section is rotatable (e.g., relative to the handle) up to 360° or more (or smaller angles, such as up to 90°, up to 180° or up to 270° degrees, or intermediate angles) about its longitudinal axis for exposing the cutting blade to different tissue areas surrounding, or partially surrounding, the cutting section, as required. Additionally or alternatively, the shielding section of the cutting section is rotatable about the longitudinal axis for exposing different sections of the cutting blade to the surrounding tissue. Additionally, the probe is further adapted to maneuver the cutting section including the rotary cutting blade into tissue regions inaccessible with straight instruments, for example, the neuroforamen in the spinal column; the acromion, humerus, and scapula in the shoulder; and the femur and the acetabulum in the hip. In some embodiments, maneuvering includes introducing the probe into an organ from an anterior side of the organ for reaching a posterior side of the organ, or inversely, introducing the probe from the posterior side of the organ for reaching the anterior side. Additionally, maneuvering may include bending the cutting section and/or rotating the cutting section for exposing the cutting blade to the tissue cutting area. Optionally, the probe may be used for removing bone spurs, and for surface preparation (decortication) for reconstructing ligament-bone attachments. In some embodiments, the cutting section may include extendible side supports which press against the tissue surrounding the cutting area for preventing torsion of the cutting section during cutting. Optionally, the side support may include a wing shape.

In an exemplary embodiment of the invention, the cutting section is replaceable with a cutting section of other degree of roughness, for example, to smooth a cut section.

In an exemplary embodiment of the invention, cutting in the spine includes advancing the tip of a probe to a spinal canal and activating the forward cutter to cut into bone. The probe may then be bent and advanced into the cut channel, remaining between the ligament and the bone or wholly within the bone. As the probe is advanced, the lateral cutting section can be used to cut against the bone. The probe can then be advanced and bend again, as needed. Optionally, this process is under control of a user who senses the resistance of the bone to cutting, for example, by an indicator (e.g., a visual or acoustic torque indicator) or based on the feel of the instrument or its sound.

In some exemplary embodiments, the cutting section is flexible and bendable for reaching the otherwise inaccessible regions. Optionally, the cutting section is axially bendable so that a distal tip of the cutting section forms an angle α ranging from −270° to 270° relative to a longitudinal axis of the probe handle, for example, −230°, −200°, −150°, −90°, 0°, 90°, 150°, 200°, 230°. Optionally, the cutting section is bendable in three-dimensional space (x-y-z planes). In some embodiments, the bending is controlled by a user and may be varied as the user cuts through the tissue. Alternatively, the cutting section is rigid and is connected in the probe by means of an articulating joint for allowing the cutting section to be positioned in three-dimensional space at an angle γ ranging from is −130° to 130°, for example, −90°, −45°, 0°, 45°, 60°, 90°.

Alternatively, the cutting section is rigidly connected in the probe at a predetermined angle β ranging from 30° to 150° relative to the longitudinal axis of the probe handle, for example, 45°, 60°, 75°, 90°, 105°, 115°, 130°, 145° or intermediate values.

In some embodiments of the invention, the bending is such that the cutting shape is concave along the longitudinal axis. In some embodiments, the bending is convex. In some embodiments, the bending is both concave and convex, e.g., at different portions. Optionally or alternatively, bending in the plane of the cutting section is provided.

In an exemplary embodiment of the invention, the bending is between two cutting edges of the cutting section, for example, if the cutting section includes a flexible blade, or if multiple blades are provided and bending is between them. In an exemplary embodiment of the invention, the bending is at a distal end of the device (e.g., within 1-5 cm from its end, for example, 2 or 3 cm), but optionally not in the bending section.

In some embodiments, all the cutting section is bendable. In others, only certain parts thereof are designed to bend.

In some embodiments of the invention, for a flexible or for a rigid cutting section, a telescoping cutter is provided.

In some embodiments, abrasive heads or other tissue removal means are provided instead of or in addition to cutting edges.

In some exemplary embodiments, the rotary cutting blade rotates about a longitudinal axis of the probe. The cutting blade is sheathed inside the cutting section which protectively shields surrounding tissue from inadvertent cutting while allowing selective and directional protruding of cutting edges for tissue cutting. Optionally, the cutting edges protrude from the cutting section between 0.1 mm to 4 mm, depending on the type of tissue to be removed. For example, the cutting edge may protrude 0.3 mm, 0.6 mm, 0.9 mm, 1.2 mm, 1.8 mm, 2.3 mm, 2.9 mm, 3.3 mm, 3.5 mm, 3.8 mm. In some embodiments, a blade control mechanism varies the protrusion of the cutting edges for controlling a tissue cutting rate and/or a tissue cutting amount and/or size. Optionally, the protrusion of the cutting edges may be varied along a length of the cutting blade for varying a tissue cutting rate along the cutting section and/or a tissue cutting amount and/or size in the tissue cutting area.

In some exemplary embodiments, the cutting section includes a window through which the cutting edges protrude for cutting tissue. Optionally, a retractable cover may be placed over the window for covering the cutting edges and preventing possible organ damage while the probe is directed to the area of tissue removal, and while removed from the area. The retractable cover may be positioned inside the cutting section and may be slidingly rotated about the longitudinal axis of the cutting end for covering and uncovering the window. Alternatively, the retractable window cover may be slid along the longitudinal axis of the cutting section for covering and uncovering (wholly or partially) the window. Additionally or alternatively, the retractable cover is adapted to cover part of the window for concealing a portion of the cutting edges which would otherwise protrude through the window, for reducing a size of the tissue cutting area.

An aspect of some embodiments of the present invention relates to a surgical probe having a flexible cutting section with a bending point between two cutting edges, for example, between two cutting wheels and/or between a lateral cutting section and a forward cutting section. In some exemplary embodiments, the rotary cutting blade includes a plurality of axially arranged cutting wheels having circumferentially-positioned cutting edges and adapted to rotate about the longitudinal axis of the probe; for example, 2 cutting wheels, 3 cutting wheels, 5 cutting wheels, 12 cutting wheels, or more. Using a plurality of cutting wheels provides for a cutting blade with greater flexibility compared with that of a single long flexible cutting blade, and at a potentially lower manufacturing cost. Optionally, a direction of cutting may be better controlled using multiple cutting wheels. Optionally, a relative position of each cutting wheel, relative to the longitudinal axis of the probe handle, varies as the cutting section is flexed through the angle α. In some embodiments, the cutting wheels may be of a same diameter while in other embodiments one or more cutting wheels may have a diameter different than that of other cutting wheels. Optionally, the cutting wheels along the tip may vary in width, type of cutting blade, material, blade and groove design, for potentially better handling of different types of tissues, better disposal of the cut tissue, and the like. Alternatively, the rotary cutting blade is a single helically shaped blade having a continuous spiraling cutting edge. Optionally, the helical shaped cutting blade is flexible and bends together with the cutting section through the angle α. Alternatively, the rotary cutting blade is a single cylindrically shaped blade and has a spiraling cutting edge. Optionally, the cylindrically shaped cutting blade is flexible and bends together with the cutting section through the angle α. In some embodiments, the spiraling cutting edge(s) may serve to transport the cut tissue in a proximal direction away from the tip. In some embodiments, the continuous rotating cutting blade may include a fixed shape and/or geometry along the rotation axis. Alternatively, the blade may include a graduated variation in diameter, for example, conical-helical shape. Additionally or alternatively, the blade may include a graduated variation of pitch, for example, the distance between windings varies. Additionally or alternatively, the blade may include a graduated variation of blade geometry for handling different types of tissues In some exemplary embodiments, the rotary cutting blade is made of a hardened biocompatible material and may include a steel or metal alloy such as, for example, hardened stainless steel or other hardened metal. Alternatively, for a non-bending rotary cutting blade, a ceramic material may be used. Alternatively, the cutting wheels may include the ceramic material A length of the rotary cutting blade may range from 1 mm to 100 mm, for example, 2 mm, 5 mm, 7 mm, 11 mm, 25 mm, 50 mm, 75 mm. An outer diameter of the rotary cutting blade may range from 0.5 mm to 6 mm, for example, 1 mm, 2 mm, 3 mm, 4 mm, 5 mm.

In some exemplary embodiments, the flexible cutting section includes a flexible base with a plurality of attached supports for supporting a flexible drive shaft. The flexible drive shaft may be made from material such as a twisted or wound stainless steel cable, a helical spring, or an assembly of springs and/or cables, and may include a conduit for transferring fluids through the conduit. A diameter of the conduit in the drive shaft may range from 0.3 mm to 2.5 mm, for example, 0.8 mm, 1.2 mm, 1.5 mm, 1.8 mm, 2.2 mm. The rotary cutting blade includes the plurality of cutting wheels which are rotatably attached to the drive shaft. Alternatively, the supports are interconnected by flexible members, for example, springs or elastomeric material, for providing flexibility to the cutting section. Alternatively, the rotary cutting blade includes the flexible helical-shaped blade. Alternatively, the rotary cutting blade includes the flexible cylindrically shaped blade. Alternatively, the flexible cutting section includes a flexible housing having grooves which provide flexibility.

In some exemplary embodiments, the probe includes a movement mechanism for moving the cutting section. Optionally, bending may be effected by pulling a wire which extends from the handle through the probe to the cutting section. Alternatively, the movement mechanism moves the cutting section attached to the articulating joint. Optionally, the movement mechanism includes a push/pull rod which runs through the probe and is operated by a lever. Optionally, the lever is in the handle. In some embodiments the movement mechanism rotates the probe shaft and/or cutting section about their longitudinal axis. In some embodiments, the movement mechanism includes motors for performing some or all of the moving actions (bending, rotating, articulating).

In some exemplary embodiments, the rotary cutting blade is rotated by the drive shaft connected to a motor. A rotational speed of the cutting blade may range from 100 RPM (revolutions per minute) to 30000 RPM or more, for example, 500 RPM, 200 RPM, 8000 RPM, 15000 RPM, 25000 RPM, 35000 RPM, 50000 RPM. The motor may be an electrically operated motor powered by AC (alternating current) or DC (direct current), for example, with batteries. Alternatively, the motor is a pneumatically operated motor. Alternatively, the cutting blades are hydraulically driven by a relatively high pressure fluid circulated through the probe. Optionally, the drive shaft is flexible and bends together with the cutting section through the angle α. In some embodiments, the surgical probe may be a hand-held device.

In some exemplary embodiments, the probe shaft is hollow and includes an internal lumen for accommodating the drive shaft. A cross-sectional outer diameter of the probe shaft may range from 1 mm-6 mm, for example, 2 mm, 3 mm, 4 mm. An internal lumen diameter may range from 0.5 mm-2.5 mm, for example, 1 mm, 1.5 mm, 2 mm. A length of the probe shaft may range from 30 mm-500 mm, for example, 50 mm, 80 mm, 120 mm, 150 mm, 190 mm, 250 mm, 325 mm, 450 mm. Optionally, the longer lengths of probe shaft enable tissue cutting along the length of bones. In some embodiments, the probe shaft is made of a rigid biocompatible material. Optionally, the rigid probe shaft includes the flexible cutting section. Alternatively, the probe shaft is made of a flexible biocompatible material, for example, Nitinol, and includes the flexible cutting section.

In some exemplary embodiments, the probe shaft includes a conduit for delivering a biocompatible and/or biodegradable fluid to the tissue removal area. Optionally, the fluid includes a medicinal fluid for administering a drug to the tissue area, for example an antibiotic. Additionally or alternatively, the fluid includes a cleaning fluid for flushing the tissue cutting area for allowing improved imaging of the area. Additionally or alternatively, the probe shaft includes a conduit for removing cut tissue out of the body, for example by connecting an aspiration device to the probe. A fluid flow rate through the conduits may range from between 0.1 cc/sec-2 cc/sec, for example, 0.5 cc/sec, 1 cc/sec, 1.5 cc/sec. Additionally or alternatively, the probe shaft includes a conduit for transporting surgical or other medical devices to the tissue cutting area. Optionally, the internal lumen may serve some or all the above functions of the conduits. Additionally or alternatively, a conduit in the drive shaft may serve some or all of the above functions. In some embodiments, the conduit may have a continuous passage to the rotating blade such that the fluid flows from the probe shaft to the rotating blade and optionally, through openings in the blade to the surgical site. Additionally or alternatively, aspiration is done through the openings in the blade and through the conduit.

In some exemplary embodiments, the probe includes a medical imaging device for allowing tracking of the position of the probe inside the body. The imaging device may include tracking means such as, for example, an optical system on its distal tip to allow imaging of the tip proximity, for example for video imaging or infrared imaging; a magnetic transmitter or receiver where the other of transmitter or receiver is located outside the body; a radiofrequency transmitter or receiver where the other of transmitter or receiver is located outside the body; an ultrasound transmitter or receiver where the other of transmitter or receiver is located outside the body.

In some exemplary embodiments, the probe is inserted into the body and approximated to the tissue cutting area through a needle. Alternatively, the probe is inserted through a cannula. Alternatively, the probe is inserted through a working channel of an endoscope. Additionally or alternatively, the probe may be directed to the tissue cutting area by means of a guidewire connecting the probe. Optionally, an imaging device such as an endoscope, or similar, is used to track the position of the probe.

In some exemplary embodiments, the probe automatically regulates a rate of tissue cutting based on detection of a signal, optionally a feedback signal, associated with nerve activity or resistance of the tissue to being cut. Optionally, the detection is by electromyography or using other methods known in the art, with a controller in the probe controlling probe operation responsive to a signal received from an externally connected electromyogram. Additionally or alternatively, the controller automatically regulates an amount and/or size of tissue cutting based on the detected mechanical and/or physiological signal. Additionally or alternatively, the controller controls a cutting speed and/or a cutting torque responsive to a sensor in the probe sensing tissue information which may include a type of tissue being contacted, a length of tissue being contacted, a termination of the tissue being contacted. Optionally, the controller notifies the physician responsive to the detection through a visual and/or audible signal.

An aspect of some embodiments of the present invention relates to a surgical probe including a frontal cutting tool for enabling the probe to frontally penetrate under tissue. In some embodiments, the frontal cutting tool is included in a distal tip of the probe. Optionally, the tip is followed by a cutting section for laterally cutting into tissue. Optionally, the cutting section includes a rotary cutting blade. Alternatively, the cutting section includes a rasp (for filing the tissue). The frontal cutting tool is adapted to open a path under the tissue for inserting the tip followed by the cutting section. This feature may be particularly advantageous in applications where a natural cavity adjacent to the tissue cutting area is not available for insertion of the probe (for example, when tissue growth in the spinal cavity between the neuroforamen wall and the spinal cord completely blocks the canal so that an instrument cannot be inserted without contacting the spinal cord). Optionally, the frontal cutting tool is a rotary cutting blade. Rotary motion causes a relative movement of the blade with the tissue to be cut, and the penetration of the blade into the outer surface of the tissue cuts small chips of tissue which are separated from the remaining of the tissue. Such penetration is initially achieved using normal forces the blade applies on the tissue which may vary from 10 s-100 s mN for eroding to 10 s N in cutting. Alternatively, the frontal cutting tool includes any other type of tissue removal tool suitable for penetrating into the tissue, for example, a burr, a drill bit, a rasp. Additionally or alternatively, the tip may include a rotating or vibratory element having a rough surface texture (abrasive) for eroding the tissue for allowing the tip to frontally penetrate into the tissue.

In an exemplary embodiment of the invention, a same power source, e.g., possibly including a shared drive shaft, is used for lateral and forward cutting sections. Optionally, some axial motion of the drive shaft is provided to assist in the cutting.

An aspect of some embodiments of the present invention relates to a surgical probe having a cutting section for lateral cutting into tissue and a frontal cutting tool for enabling the probe to frontally penetrate under the tissue.

An aspect of some embodiments of the present invention relates to a kit including the surgical probe for use in the treatment of spinal stenosis Additionally or alternatively, the kits may be used for treating other conditions requiring tissue removal from body organs, for example, in the shoulder or the hip. In some embodiments, the probe is a single-use device which is disposed of following surgical use. Alternatively, the probe shaft including the cutting section, the cutting blade, and the drive shaft are disposed of and replaced following one-time use. Alternatively, the cutting section including the cutting blade and the drive shaft are disposed of and replaced following one-time use. Optionally, the cutting section includes the frontal cutting tip. Alternatively, only the rotary cutting blade and the drive shaft are disposed of and replaced. Optionally, the frontal cutting blade is disposed of and replaced.

An aspect of some embodiments of the present invention relates to a method of forward cutting under body tissue. Optionally, forward cutting of the body tissue is followed by removal of the tissue through lateral cutting. Optionally, the method includes penetrating into an under-portion of the tissue using a frontal cutting tool and forming a cavity wherein a lateral tissue cutting tool may be accommodated. Optionally, once inside the cavity, the lateral tissue cutting tool may laterally cut away at the tissue in a direction towards a tissue surface (external direction). Additionally or alternatively, the lateral tissue cutting tool may laterally cut in a direction away from the tissue surface (internal direction), deeper into the tissue. Lateral cutting may include any one or combination of cutting (with a blade), rasping, burring, and eroding. Forward cutting may include any one or combination of cutting, drilling, burring, eroding (through abrasion), and rasping.

For example, such cutting may be used with arthroscopic or endoscopic tools, for example, for cutting bone under a ligament or bone under cartilage or muscle.

The devices disclosed herein, in some embodiments, are technically advantageous over the prior art as they do not require insertion into natural cavities adjacent to tissue cutting areas for cutting tissue, as required by the prior art. For example, in treating spinal stenosis prior art teaches inserting the surgical device into the neuroforamen for accessing the tissue cutting area. An additional advantage is that use of the devices require only one incision be made in the body, potentially simplifying the surgical procedure and resulting in faster patient post-surgical recuperation.

Other potential advantages, in some exemplary embodiments, rest in the possible preventing of ligament inflammation by attempting to not cut ligaments. Although some embodiments may include ligament cutting, other embodiments may not require such cutting. Additional advantages, in some exemplary embodiments, is that the blade bends to substantially match the shape of the surface of the bone. Other advantages include, in some exemplary embodiments, urging the cutting surfaces of ligaments or other tissues against the bone surface.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Surgical Probe with Flexible Cutting Section

Figure 1B:
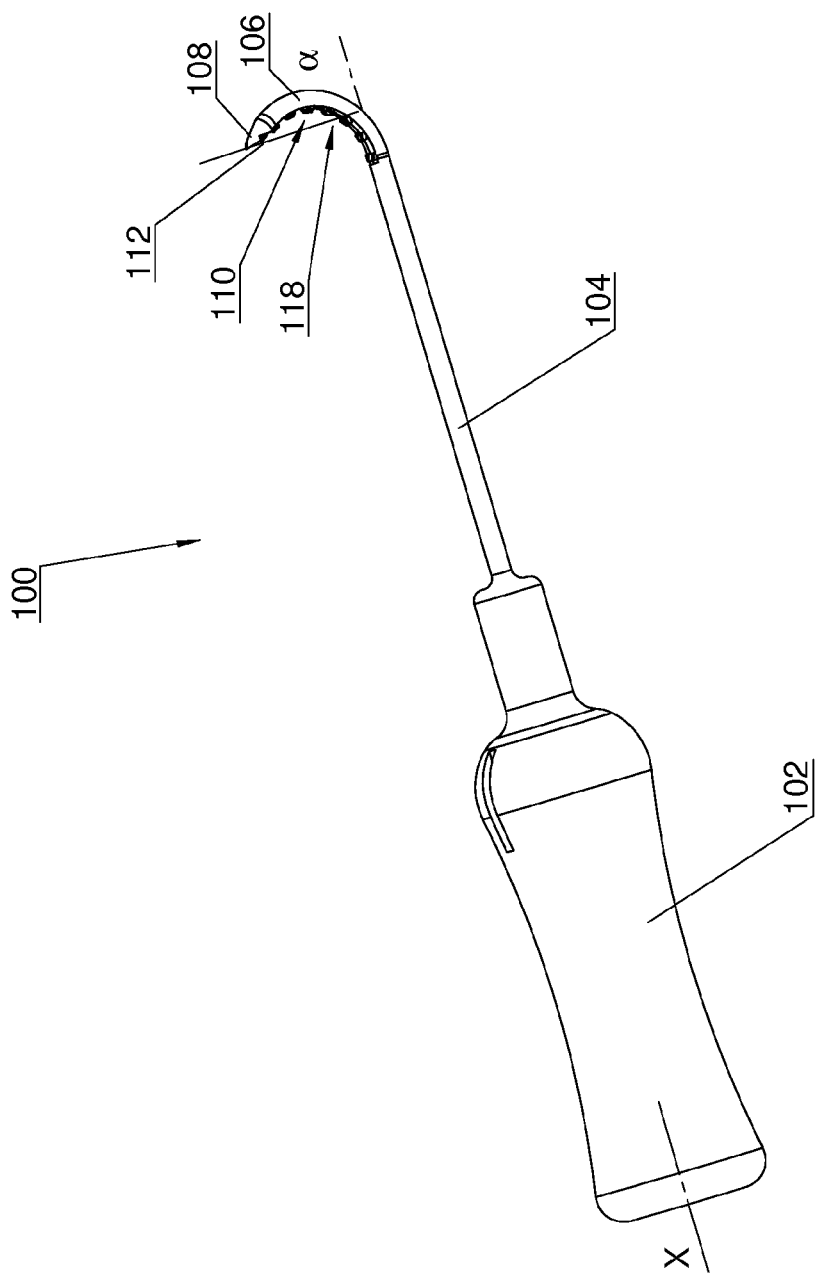
FIG. 1B schematically illustrates a perspective view of an exemplary surgical probe having a relatively large flexed distal end, according to an embodiment of the present invention.

Reference is now made to FIGS. 1A and 1B which schematically illustrate perspective views of an exemplary minimally-invasive surgical probe 100, according to an embodiment of the present invention. Probe 100 includes a proximal handle 102, and a probe shaft 104 proximally connected to the handle and having a flexible cutting section 106 including a tip 108 at a cutting end. Cutting section 106 includes a rotary cutting blade 110 for laterally cutting tissue. Optionally, cutting section 106 includes a frontal cutting blade 112 in tip 108 for forward cutting under tissue. In FIG. 1A, probe 100 is shown with cutting section 106 slightly flexed, tip 108 at a small angle $\alpha$ relative to a longitudinal axis "x" of handle 102. In FIG. 1B, probe 100 is shown with cutting section 106 flexed upwards, tip 108 at a relatively large angle $\alpha$ relative to a longitudinal axis "x" of handle 102.

In some exemplary embodiments, handle 102 houses a motion controller 114 for controlling movement of components in the probe, including bending of cutting section 106 and operation of rotary cutting blade 110 and optionally frontal cutting blade 112. Optionally, motion controller 114 is adapted to rotate probe shaft 104 by up to 360°, shown by exemplary arrow A. Additionally or alternatively, motion controller 114 is adapted to rotate cutting section 106 by up to 360°, shown by exemplary arrow B. Motion controller 114 may include motorized means for controlling any one or all of bending cutting section 106, rotating the cutting section and/or probe shaft 104, operating rotating cutting blade 110 and frontal cutting blade 112. Alternatively, motion controller 114 may include a mechanical mechanism which is manually operated by a user of probe 100, for example by pulling a wire to cause bending of cutting section 106 or turning a knob for rotating the cutting section and/or probe shaft 104. In some embodiments, motion controller 114 may include an electronic controller and/or a hydraulic controller. In some embodiments, motion controller 114 controls movements responsive to signals received from a foot pedal operated by the physician.

In some exemplary embodiments, handle 102 houses a controller 116 for controlling other operations not handled by motion controller 114. These operations may include, for example, imaging, aspiration, and irrigation, as well as interfacing with externally connected equipment associated with these operations. In some embodiments, control circuitry 116 and motion controller 114 are integrated as one unit.

Figure 2:
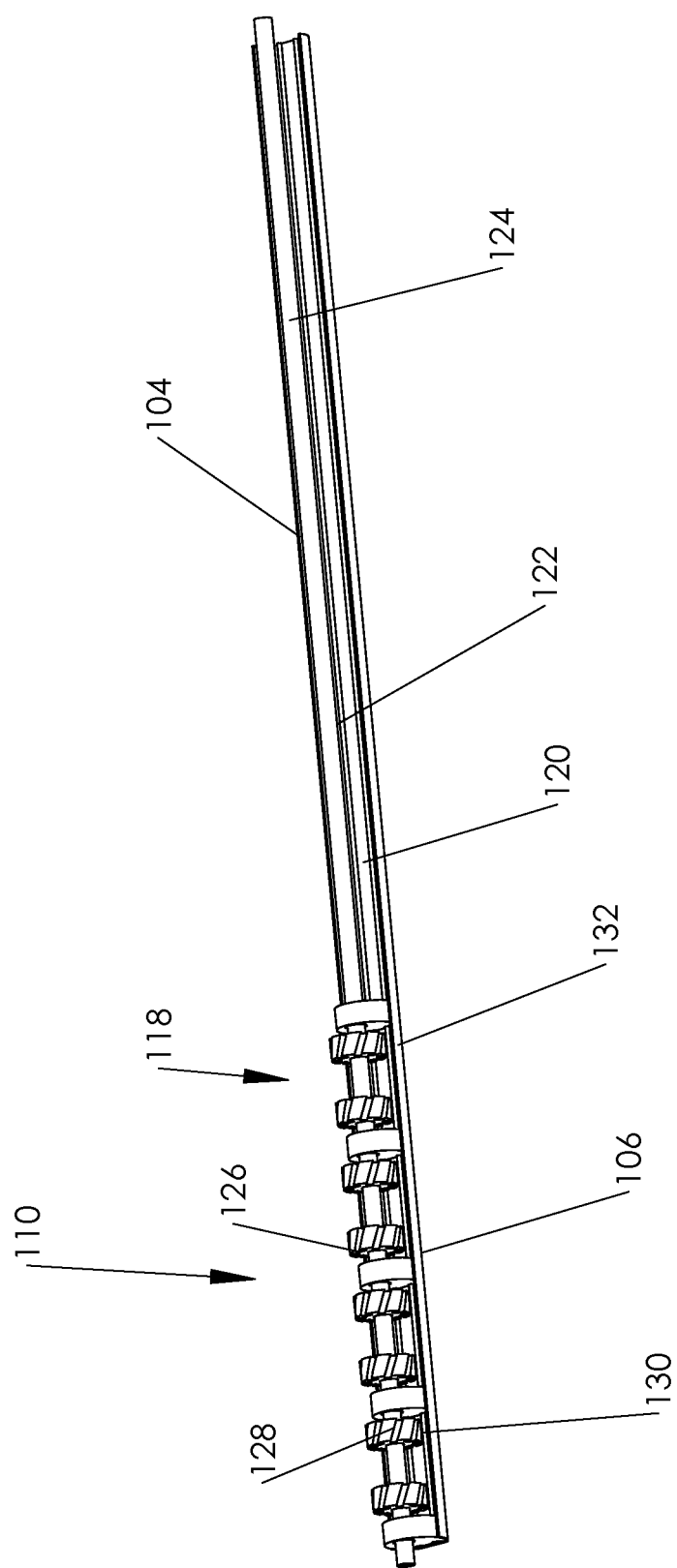
FIG. 2 schematically illustrates a perspective view of a probe shaft in a relatively non-flexed configuration and including a rotary cutting blade having rotary cutting wheels, according to an embodiment of the present invention.

Reference is now also made to FIG. 2 which schematically illustrates a perspective view of probe shaft 104 in a relatively non-flexed configuration and including rotary cutting blade 110 having rotary cutting wheels 126, according to an embodiment of the present invention. Optionally, probe shaft 104 is rigid along a portion of its length to flexible cutting section 106. Alternatively, probe shaft 104 is flexible along its entire length.

In some exemplary embodiments, probe shaft 104 is cylindrical in shape and includes an inner lumen 120 which extends from handle 102 to tip 108. Extending along a length of inner lumen 120 is a drive shaft 122 which is proximally connected to a motor in motion controller 114 and distally connects to rotary cutting blade 110 for imparting unidirectional rotary motion to the cutting blade. Optionally, drive shaft 122 is flexible and is adapted to bend with cutting section 106.

In some exemplary embodiments, delivery of fluids to the tissue cutting area is done through inner lumen 120. The fluid may be supplied from a fluid source external to probe 100, optionally connected to the probe through a connector (not shown) in proximal handle 102. The connector may be adapted to connect to a syringe which may optionally form part of an intravenous (IV) fluid delivery device or other suitable fluid supply source. Additionally or alternatively, aspiration of cut tissue is done through inner lumen 120. Optionally, an external aspiration device is connected to the connector in handle 102. Optionally, aspiration and/or fluid delivery may be done through a conduit 124 in probe shaft 122. In some embodiments, rotary cutting blade 110 and drive shaft 122 are removable for enabling surgical and/or other devices to be inserted through inner lumen 120 into the tissue cutting area.

In some exemplary embodiments, shielding between cutting edges 128 in cutting wheels 126 and tissue areas which are not to be cut is provided by the sheath-like enclosure of cutting section 106 wherein the only exposure of the cutting edges to an exterior of probe shaft 104 is through a window 118. Cutting section 106 includes a cutting section wall 132 which partially encloses rotary cutting blade 110 and prevents cutting edges 128 from coming into contact with tissue. Optionally, cutting edges 128 in cutting wheels 126 protrude from a side of probe shaft 104 through window 118 for cutting tissue. A retractable cover 130 may be rotatably adjusted to cover window 118 for preventing contact between tissue and rotary cutting blade 110 while probe 100 is inserted through the body into the tissue cutting area, and when removed from the tissue cutting area. Optionally, retractable cover 130 may be rotatably adjusted to partially cover window 118 for controlling an exposure area of cutting edges 128 to the tissue cutting area.

Figure 3A:
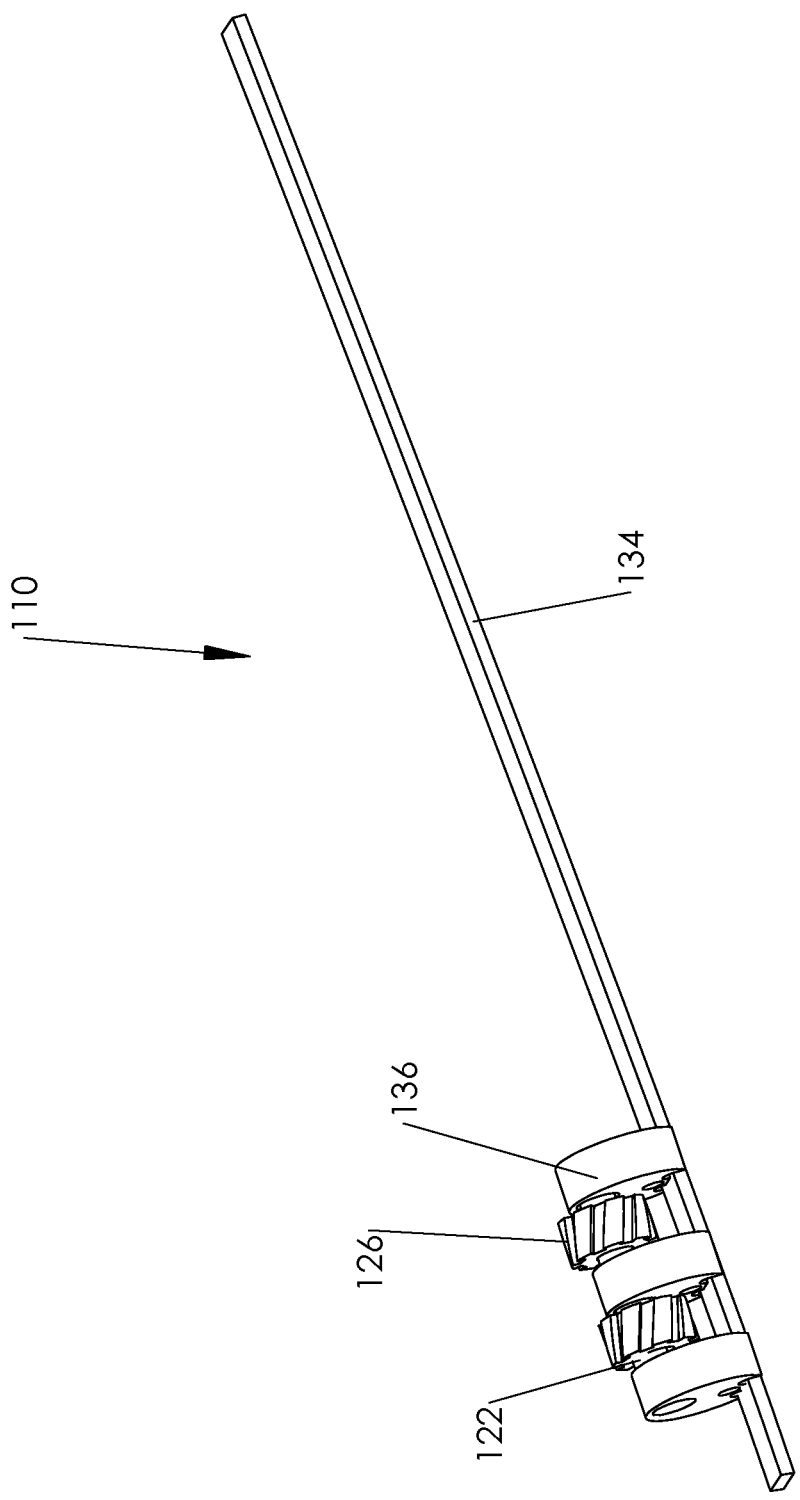
FIG. 3A schematically illustrates a perspective view of a section of a flexible rotary cutting blade in a relatively straightened configuration, according to an embodiment of the present invention.
Figure 3B:
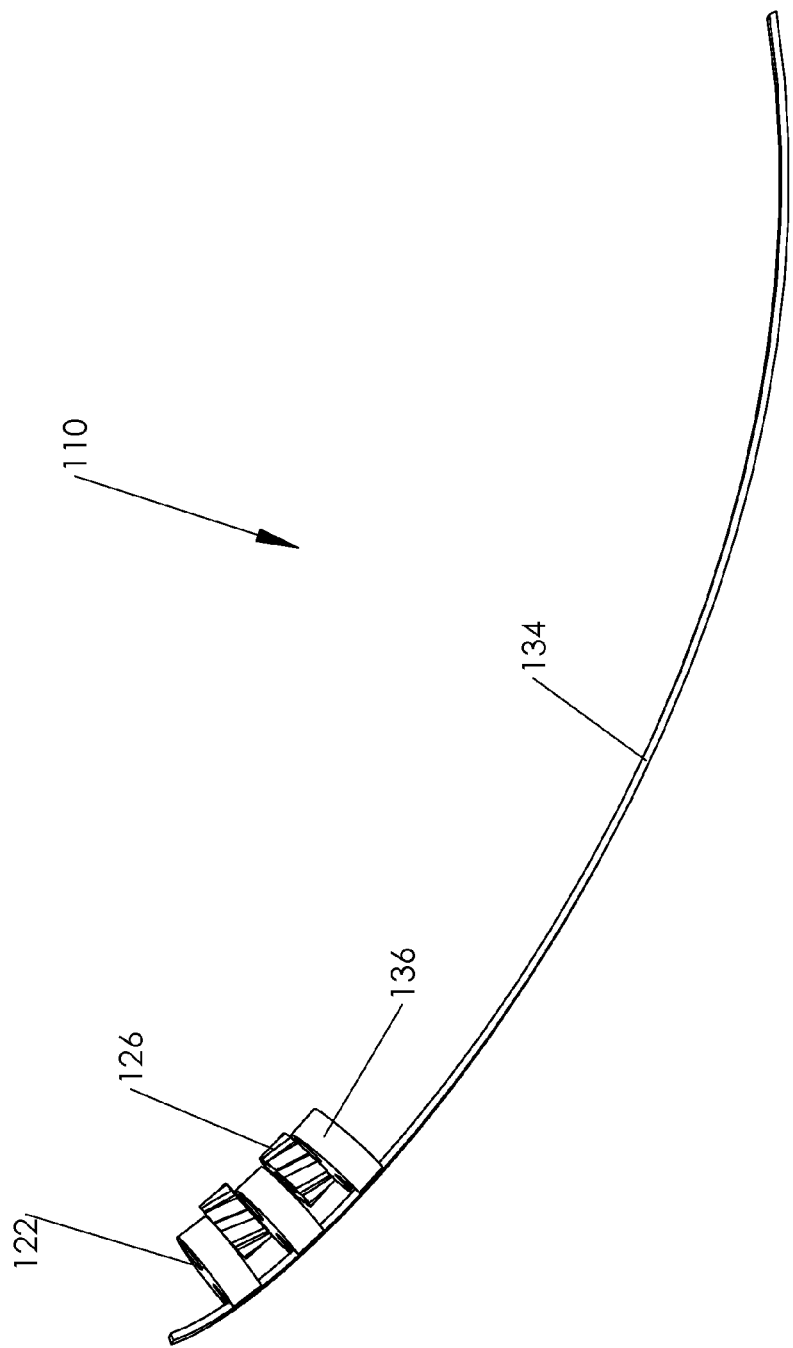
FIG. 3B schematically illustrates a perspective view of a section of a flexible rotary cutting blade in a flexed configuration, according to an embodiment of the present invention.

Reference is now also made to FIGS. 3A and 3B which schematically illustrate a perspective view of a section of a flexible rotary cutting blade 110, according to an embodiment of the present invention. Rotary cutting blade 110 is shown having rotary cutting wheels 126 connected to flexible drive shaft 122 and supported by drive shaft supports 136. Drive shaft supports 136 are attached to a flexible base 134 adapted to bend with distal section 106 through the angle α. In some embodiments, drive shaft supports 136 and flexible base 134 include a hardened metal such as, for example, hardened stainless steel.

In FIG. 3A, rotary cutting blade 110 is shown in a relatively straightened configuration. In FIG. 3B, rotary cutting blade 110 is shown in a flexed configuration.

In some exemplary embodiments cutting section 106 is a modular unit which may be modularly fitted as a single component onto probe shaft 104. Optionally, modular fitting of cutting section 106 allows for easy installation and/or replacement of the cutting section, for example, when the blade is worn or depending on the surgical procedure to be performed (if the procedure involves the spine, the hip, the shoulder, or other organs) and the type of blade required for the procedure. Additionally, modular fitting may find practical application in a surgical probe kit including a disposable cutting section. An ordinary person skilled in the art may appreciate a potential advantage of having a surgical probe which may be used with different cutting sections.

In some exemplary embodiments, a vacuum source may be attached to surgical probe 100. Optionally, the vacuum source is connected through handle 102. Optionally, a power source may be connected to the probe 100. In some embodiments, probe 100 includes an integral battery and a motor.

Flexible Cutting Section Embodiments

Figure 4:
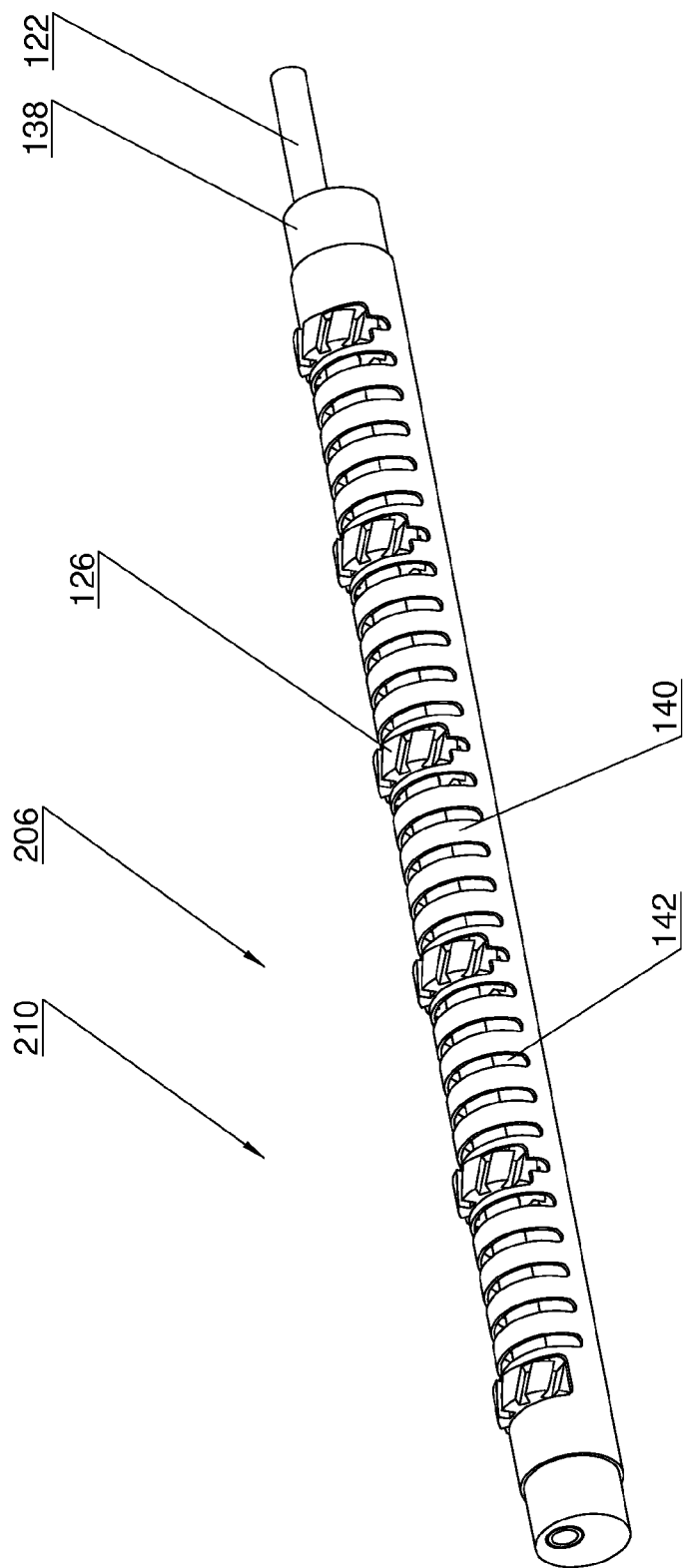
FIG. 4 schematically illustrates a perspective view of a rotary cutting blade, according to some embodiments of the present invention.
Figure 5:
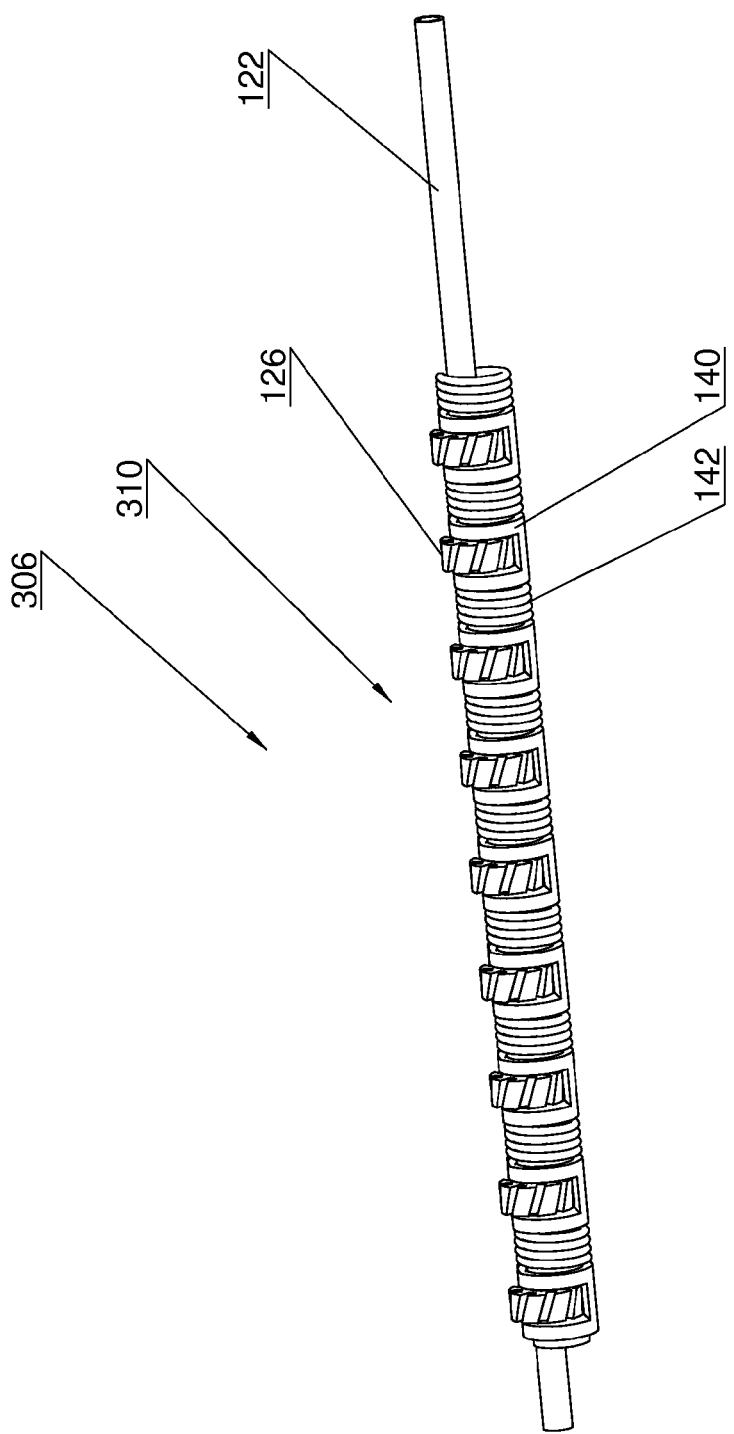
FIG. 5 schematically illustrates a perspective view of a rotary cutting blade, according to some embodiments of the present invention.

Reference is now also made to FIG. 4 which schematically illustrates a perspective view of a cutting section 206 including a flexible housing 138 and a flexible rotary cutting blade 210, according to some embodiments of the present invention. Rotary cutting blade 210 is shown having rotary cutting wheels 126 connected to drive shaft 122 inside housing 138. Housing 138 includes ribs 140 and slots 142 which allow the housing to flex together with rotary cutting blade 210 through the angle α. In some embodiments, housing 138 includes a hardened metal such as, for example, hardened stainless steel. Optionally, cutting section 206 is interchangeable with cutting section 106 and may be fitted onto probe shaft 104. Reference is now also made to FIG. 5 which schematically illustrates a perspective view of a cutting section 306 including a flexible rotary cutting blade 310, according to some embodiments of the present invention. Rotary cutting blade 310 is shown having rotary cutting wheels 126 connected to drive shaft 122 and supported by rigid drive shaft supports 140. Drive shaft supports 140 are interconnected to one another by flexible members 142 for allowing flexing of cutting section 306 through the angle α. Optionally, flexible members 142 include tension springs. In some embodiments, drive shaft supports 140 and the tension springs 142 include a hardened metal such as, for example, hardened stainless steel. Alternatively, flexible members 142 include elastomeric components. Optionally, cutting section 306 is interchangeable with cutting section 106 and 206 and may be fitted onto probe shaft 104.

Rotary Cutting Blade Embodiments

Figure 6:
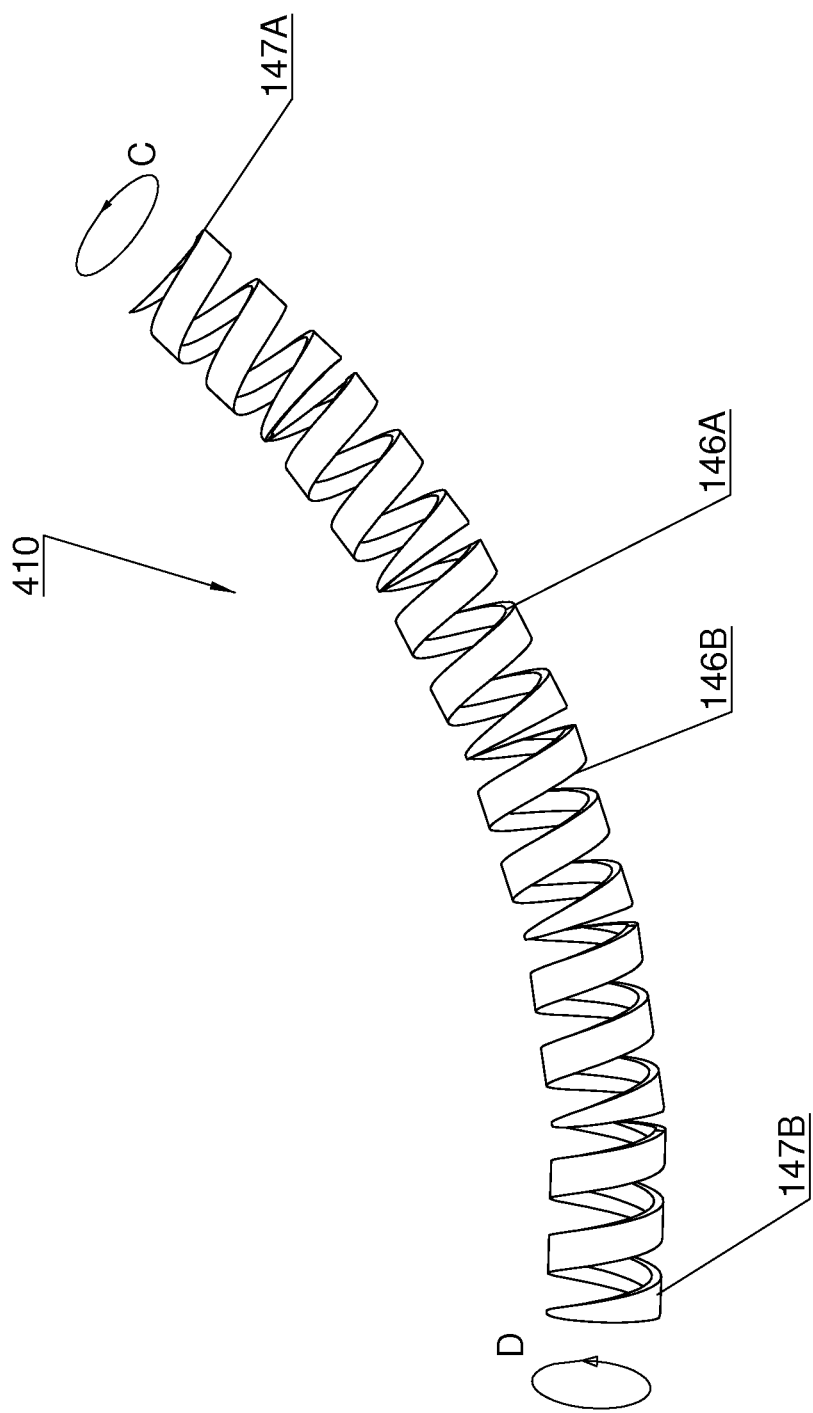
FIG. 6 schematically illustrates an exemplary perspective view of a helically shaped rotary cutting blade including a continuous spiraling cutting edge, according to some embodiments of the present invention.

Reference is now also made to FIG. 6 which schematically illustrates a perspective view of an exemplary helically shaped rotary cutting blade 410 including a continuous spiraling cutting edge 146, according to some embodiments of the present invention. Rotary blade 410 is adapted to be used in cutting section 106 and is rotatable by shaft 122 relative to the longitudinal axis of probe shaft 104 for cutting tissue (with cutting edges 146A and/or 146B). In some embodiments, cutting blade 410 includes right cutting edge 146A for cutting tissue when a right end 147A of the blade is rotated in a counterclockwise direction, as shown by arrow C. Alternatively, cutting blade 410 includes a left cutting edge 146B for cutting tissue when a left end 147A of the blade is rotated in a counterclockwise direction, as shown by arrow D. Alternatively, cutting blade 410 includes both cutting edges 146A and 146B for enabling tissue cutting independently of the direction of blade rotation. Rotary blade 410 is further adapted to bend with cutting section 106 through the angle α. In some embodiments, cutting blade 410 includes a hardened metal such as, for example, hardened stainless steel. Optionally, rotary cutting blade 410 may be used with probes 100 having non-flexing cutting sections. Optionally, rotary cutting blade 410 is interchangeable with rotary cutting blades 110-310. In some embodiments, rotary cutting blade 410 removes cut tissue from the cutting area by transporting the cut tissue spirally along the blade in a proximal direction from tip 108 towards control handle 102. Optionally, the cut tissue is aspirated through inner lumen 120 by an aspiration device (not shown) connected to probe 100.

Figure 7:
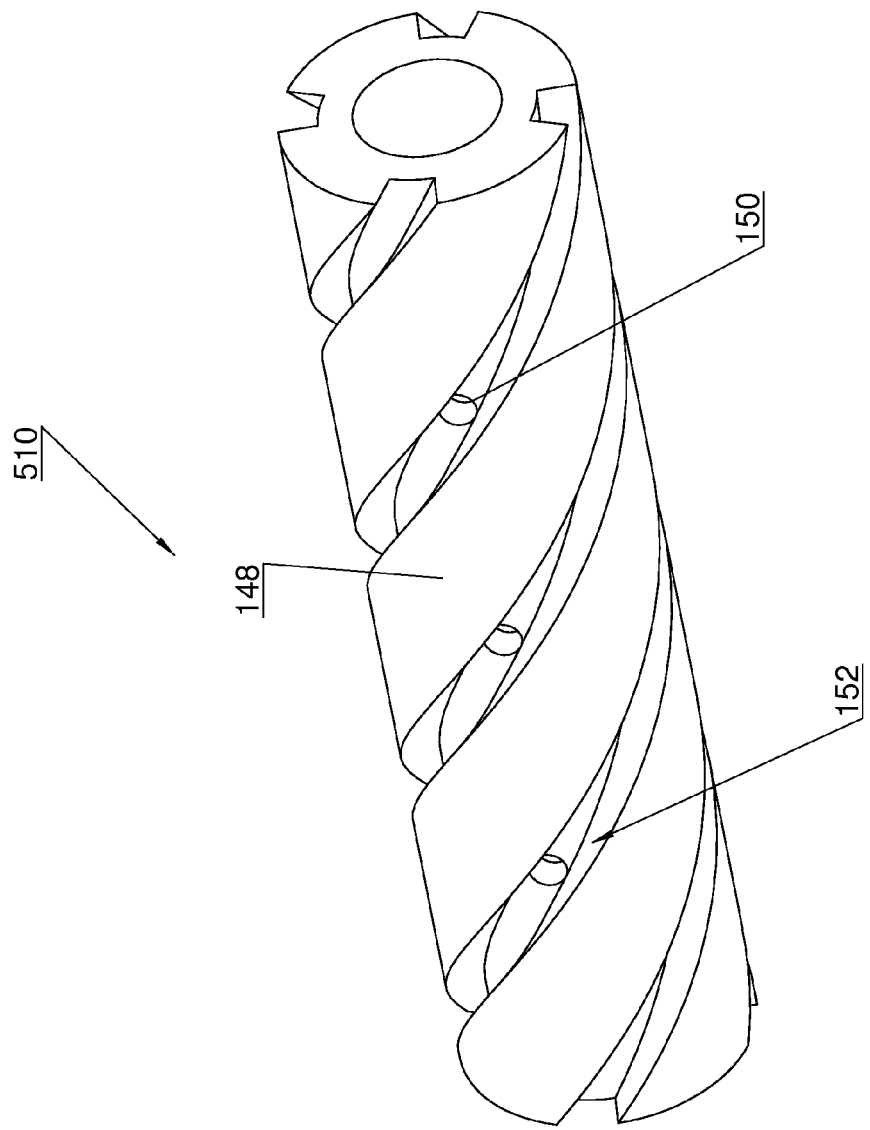
FIG. 7 schematically illustrates an exemplary perspective view of a cylindrically shaped rotary cutting blade including a continuous spiraling cutting edge, according to some embodiments of the present invention.

Reference is now also made to FIG. 7 which schematically illustrates an exemplary perspective view of a cylindrically shaped rotary cutting blade 510 including a continuous spiraling cutting edge 148, according to some embodiments of the present invention. Rotary cutting blade 510 is adapted to be used in cutting section 106 and is rotatable by shaft 122 relative to the longitudinal axis of probe shaft 104 for cutting tissue (with cutting edges 148). Rotary blade 510 is further adapted to bend with cutting section 106 through the angle α. In some embodiments, cutting blade 510 includes a hardened metal such as, for example, hardened stainless steel. Optionally, rotary cutting blade 510 may be used with probes 100 having non-flexing cutting sections. Optionally, rotary cutting blade 510 is interchangeable with rotary cutting blades 110-410. In some embodiments, rotary cutting blade 510 includes openings 150 in cutting grooves 152 through which a fluid may be administered to the tissue cutting area. Optionally, fluids in the tissue cutting area may be aspirated into inner lumen 120 through openings 150. In some embodiments, cut tissue is removed from the cutting area by transporting the cut tissue spirally along the blade inside cutting grooves 152 in a proximal direction from tip 108 towards control handle 102.

Surgical Probe with Articulating Joint

Figure 8:
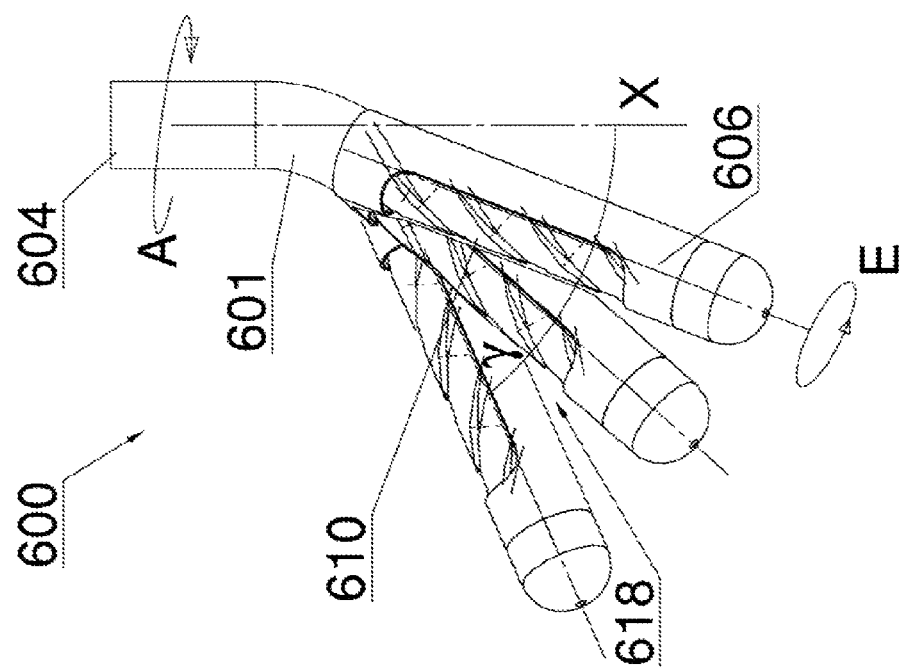
FIG. 8 schematically illustrates a perspective view of an exemplary minimally-invasive surgical probe, according to some embodiments of the present invention.

Reference is now made to FIG. 8 which schematically illustrates a perspective view of an exemplary minimally-invasive surgical probe 600, according to some embodiments of the present invention. Probe 600 includes a probe shaft 604 to which a cutting section 606 having a window 618 and a rotary cutting blade 610 is connected through an articulating joint 601. Optionally, rotary cutting blade 610 is interchangeable with rotary cutting blades 110-510. In some embodiments, probe shaft 604 and cutting section 606 are relatively non-flexible. Articulating joint 601 allows cutting section 606 to be displaced in three-dimensional space over angle γ ranging from is −130° to 130°, for example, −90°, −45°, 0°, 45°, 60°, 90°, relative to longitudinal axis "x" of a probe handle (not shown) for accessing concealed tissue regions not accessible using a straight instrument. Alternatively, articulating joint allows cutting section 606 to be displaced through angle γ along a plane defined by an x-y axes, an x-z axes, or an y-z axes. Optionally, articulating joint 601 is adapted to allow probe shaft 604 to rotate up to 360° about longitudinal axis "x". In some embodiments, cutting section 606 may be rotated about its longitudinal axis for rotating window 618 to a different tissue cutting area in the vicinity of the cutting section the rotational movement shown by arrow E. Optionally, rotating window 618 prevents moving surgical probe 600 for accessing a different tissue cutting area surrounding cutting section 606.

Surgical Probe with Fixed Cutting Section

Figure 9:
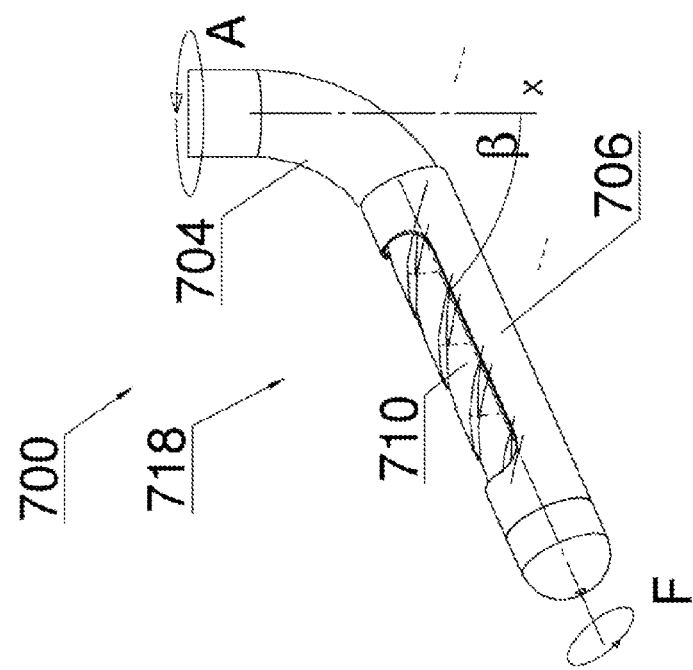
FIG. 9 schematically illustrates a perspective view of an exemplary minimally-invasive surgical probe, according to some embodiments of the present invention.

Reference is now made to FIG. 9 which schematically illustrates a perspective view of an exemplary surgical probe 700, according to some embodiments of the present invention. Probe 700 includes a probe shaft 704 to which a cutting section 706 having a rotary cutting blade 710 is rigidly connected at a predetermined angle β ranging from 30° to 150° relative to the longitudinal axis "x" of the probe handle, for example, 45°, 60°, 75°, 90°, 105°, 115°, 130°, 145°. Optionally, probe shaft 704 is rotatable clockwise and/or counter-clockwise up to 360° about longitudinal axis "x". Rotary cutting blade 710 may be interchangeable with rotary cutting blades 110-610.". In some embodiments, cutting section 706 may be rotated about its longitudinal axis for rotating window 718 to a different tissue cutting area in the vicinity of the cutting section, the rotational movement shown by arrow F. Optionally, rotating window 718 prevents moving surgical probe 700 for accessing a different tissue cutting area surrounding cutting section 706.

Exemplary Methods of Use

Figure 10:
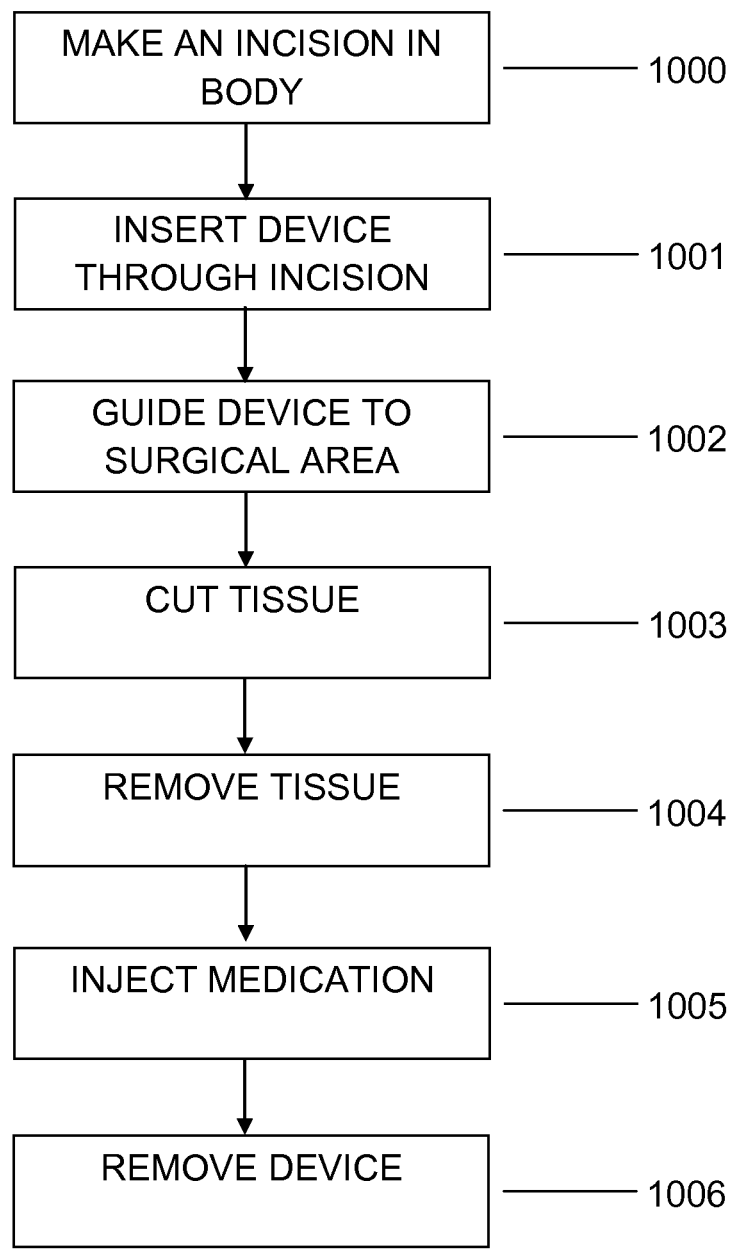
FIG. 10 illustrates a flow graph of an exemplary method of performing a minimally-invasive surgical procedure for removing tissue using the surgical probe of FIGS. 1A and 1B, according to an embodiment of the present invention.

Reference is now made to FIG. 10 which illustrates a flow graph of an exemplary method of performing a minimally-invasive surgical procedure for removing tissue using device 100, according to an embodiment of the present invention. An exemplary method for treating spinal stenosis is described further on below (see FIGS. 12A-12D).

At 1000, the physician makes an incision in the skin of a patient. Optionally, the incision is made in the vicinity of the shoulder, the hip, or the spinal column, for treating a condition in any one of these areas. A guiding tube such as a needle or an endoscopic tube is inserted through the incision and its distal end guided to the vicinity of the surgical area.

At 1001, the physician inserts probe 100 through the guiding tube into the surgical area. Prior to insertion, the physician optionally activates an imaging device in probe 100 and verifies proper imaging. Additionally or alternatively, the physician may use an endoscopic device for imaging. Optionally, the physician may have previously inserted a guide wire through the guiding tube for guiding surgical probe 100 to the tissue cutting area.

At 1002, the physician guides probe 100 to the surgical area where tissue will be cut and removed. Optionally, the physician uses frontal cutting blades 112 for penetrating under tissue, including bone tissue, to reach the tissue cutting area.

At 1003, the physician manipulates control handle 102 for positioning cutting section 106 so that window 118 faces the tissue surface to be cut. Optionally, cutting section 106 is bent for reaching a tissue cutting area not in a direct line of sight. Optionally, cutting section 106 is rotated for aligning window 118 with the tissue surface. Additionally or alternatively, probe shaft 104 is rotated. Optionally, window 118 faces an underportion of the tissue from inside a cavity opened by frontal cutting blade 112. In some embodiments, all positioning and probe adjustments are made by motion controller 114 responsive to an activation signal by the physician (for example, pressing of one or more buttons on handle 102 or on a foot pedal). Alternatively, all positioning and probe adjustments are manually effected by the physician (for example, by pulling wires, turning knobs, and the like). Optionally, retractable cover 130 is manipulated to a desired size of window opening for exposing a portion of cutting edges 128. Additionally or alternatively, s a distance cutting edges 128 in rotary cutting wheels 126 protrude out window 118 is adjusted using the blade adjustment mechanism. Once the amount of protruding cutting edges has been adjusted, the physician may proceed to cut the tissue which is to be removed. Optionally, the physician manually adjusts the cutting rate and the cutting amount. Alternatively, probe 100 automatically adjusts cutting rate and tissue amount/size responsive to a signal received from an electromyogram or by detecting a resistance in the tissue to cutting.

At 1004, the physician optionally activates an aspiration mechanism externally connected to probe 100, optionally through handle 102, for removing cut tissue and fluids from the surgical area. The cut tissue/fluids are aspirated through openings in cutting section 106 (for example, between cutting wheels 126 or through other openings in the cutting section, including window 118) into inner lumen 120 in a proximal direction towards control handle 102. Additionally or alternatively, conduit 124 in drive shaft 122 is also used for aspirating the cut tissue and fluids.

At 1005, medication such as an antibiotic, a sterilizing fluid, and/or a pain relieving medication is optionally delivered through probe 100 to areas where tissue was cut. Optionally, the medication is delivered through inner lumen 120. Additionally or alternatively, the medication is delivered through conduit 124.

At 1006, physician closes window 118 and prepares probe 100 for removal from body, including adjusting a position of cutting section 106 so that it does not interfere with probe 100 movement during the extraction. The physician guides probe 100 out of the surgical area and through the body out the guiding tube. Following probe 100 removal, the guiding tube is removed and the incision may then be closed.

The above method was described for exemplary purposes. An ordinary person skilled in the art practicing the method may find that the order of the steps may be changed, or that steps may be added or removed.

Surgical Probe Kit

Figure 11:
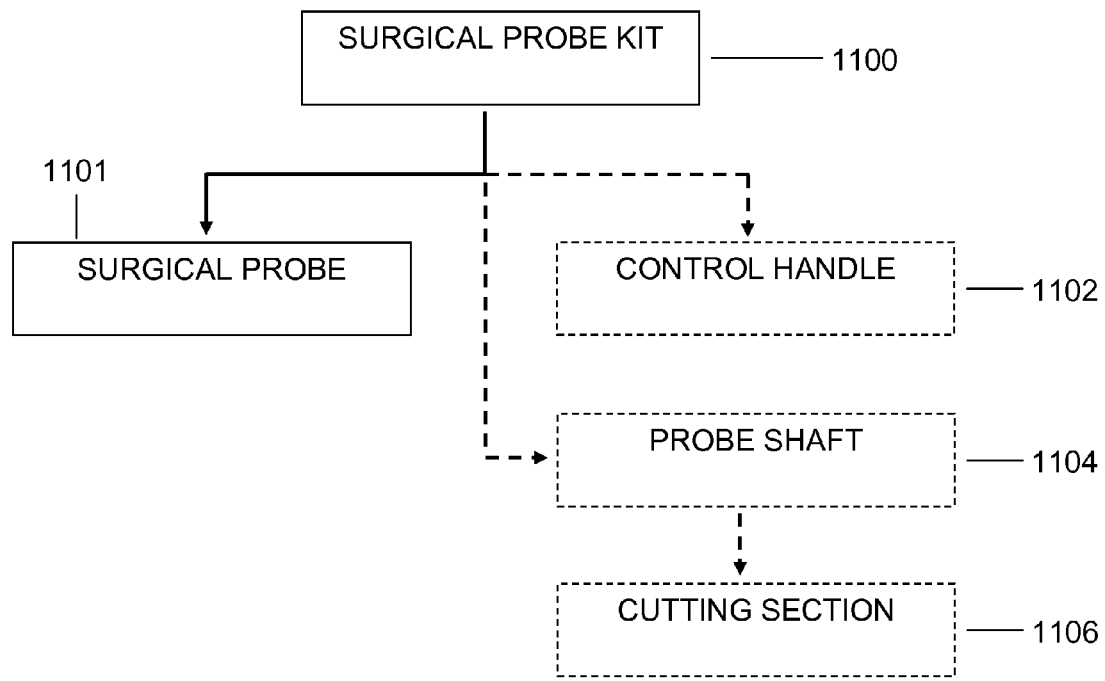
FIG. 11 illustrates a block diagram of a minimally-invasive surgical probe kit, according to some embodiments of the present invention.

Reference is now made to FIG. 11 which illustrates a block diagram of a minimally-invasive surgical probe kit 1100 for treating spinal stenosis, according to some embodiments of the present invention. Optionally, surgical probe kit 1100 may be used for treating other conditions requiring tissue removal in the spinal column, the shoulder joint, the hip joint, or other organ. Surgical probe kit 1100 includes a surgical probe 1101 having a flexible cutting section 1106 for lateral cutting of tissue. Optionally, flexible cutting section 1106 includes a frontal cutting tool for forward cutting under tissue. Optionally, surgical probe 1101 is a single-use device which is disposed of following use in a surgical procedure.

In some exemplary embodiments, kit 1100 may include a control handle 1102 and a probe shaft 1104 having a cutting section 1106 including a rotary cutting blade. Optionally, probe shaft 1104 is a single-use component which is disposed of and replaced following a surgical procedure. Alternatively, the cutting section 1106 is detachable from probe shaft 1104 and is removed and replaced following the surgical procedure. Optionally, replacement of cutting section 1106 includes replacement of the drive shaft.

Treating Spinal Stenosis

Reference is now made to FIGS. 12A-12D which schematically illustrate an exemplary method for treating spinal stenosis in a vertebral column 1200 using surgical probe 100, according to some embodiments of the present invention. Optionally, the stenosis is a foraminal stenosis. Additionally or alternatively, the stenosis is a central stenosis.

Figure 12A:
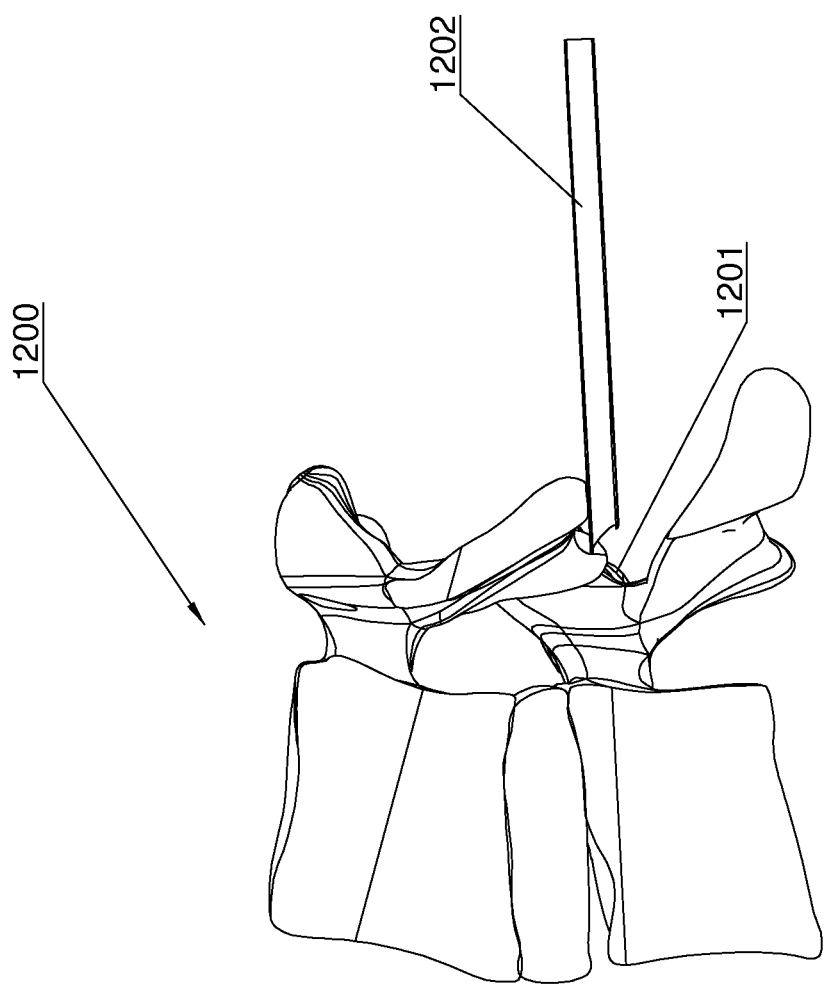
FIGS. 12A-12D schematically illustrate steps in an exemplary method for treating spinal stenosis in a vertebral column using a surgical probe, according to some embodiments of the present invention.

As shown in FIG. 12A, a needle 1202, alternatively an endoscopic tube or a trocar, is inserted through a cavity 1201 in vertebral column 1200 in proximity to the area of the stenosis.

Figure 12B:
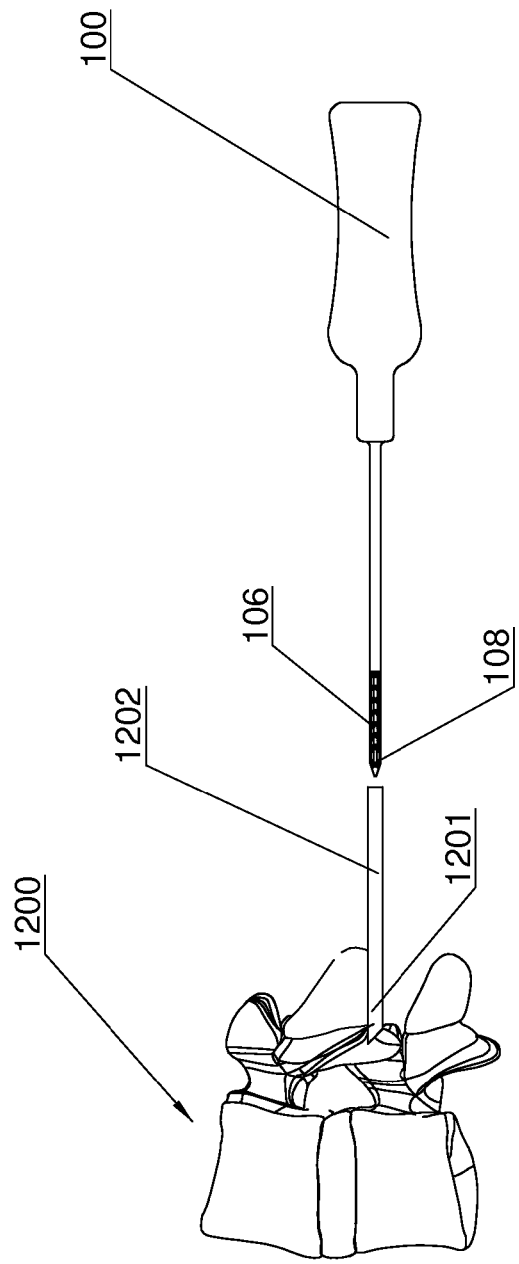

As shown in FIG. 12B, probe 100 is inserted, with cutting section 106 coaxially aligned with the longitudinal axis of the probe, into needle 1202 and advanced until distal tip 108 reaches the surgical site.

Figure 12C:
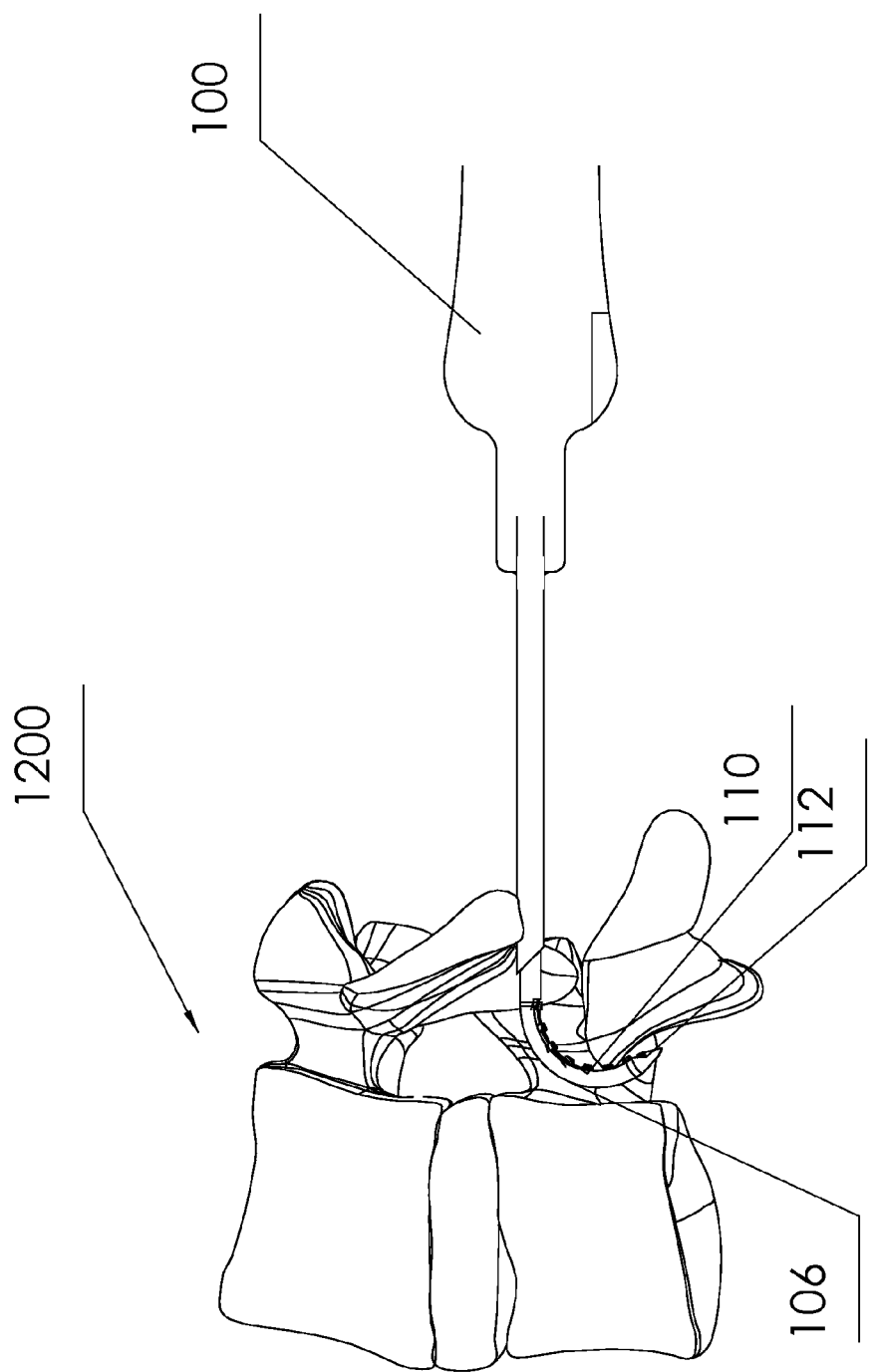
Figure 12D:
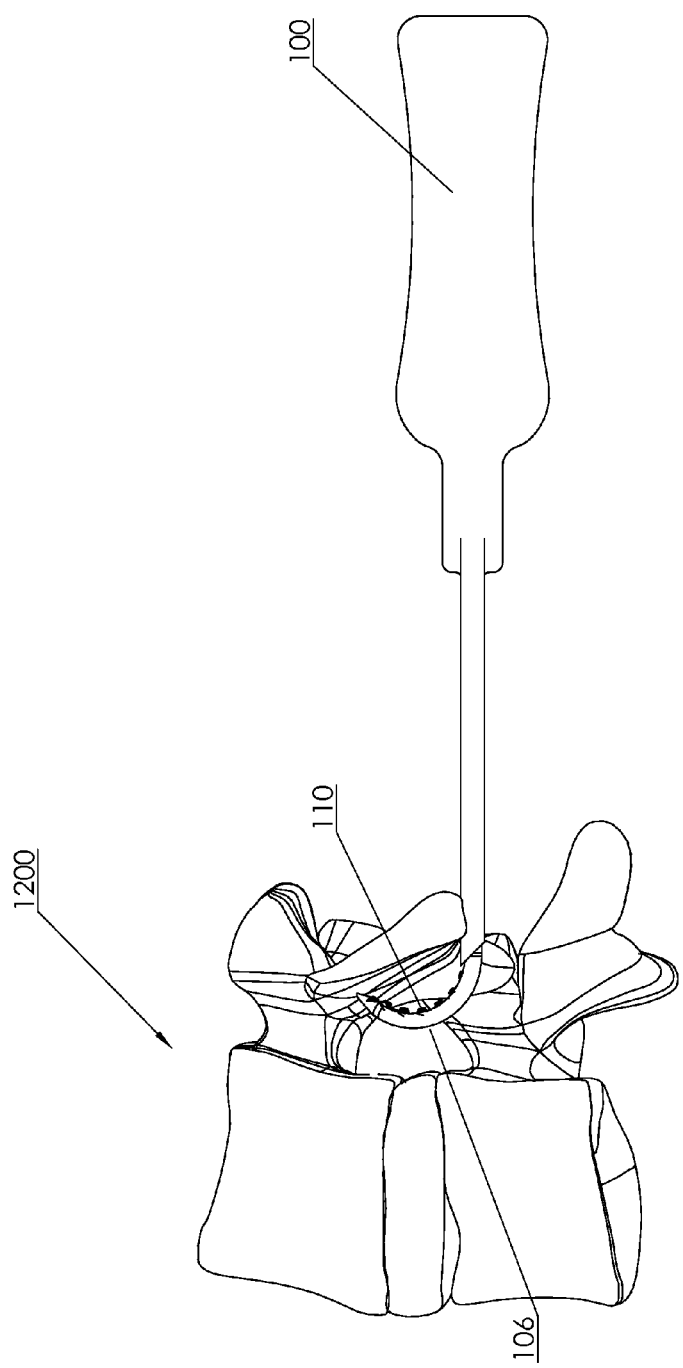

As shown in FIGS. 12C and 12D, once distal tip 108 reaches the surgical site, cutting blade 110 is operated to start cutting tissue and the irrigation and aspiration is operated to remove the cut tissue. Optionally, frontal cutting blade 112 is operated prior to operation of cutting blade 110, or alternatively, together with the cutting blade. Feedback is constantly received by the surgeon (for example, torque resistance applied on the motor) for making a decision when to advance the probe forward. Other feedback may be received using any one or any combination of light, sound, computer generated sound, vibration, x-ray imaging, or human sensory perception by feeling resistance to moving the probe or by monitoring an amount of cut tissue being washed up. Optionally, upon determining that an adequate amount of tissue has been removed in front of tip 108, the surgeon initiates bending of cutting section 106 while cutting and steering (including pushing) the device forward for advancing tip 108 into tissue areas that are not directly in front of needle 1202. Optionally, this may be done by using cutting, bending and advancing functions simultaneously until tip 108 is in the desired place. Optionally, further tissue can be removed using retraction of probe 100 with cutting section 106 bent, or rotating the device over its longitudinal axis, or a combination of both movements. Following removal of all the tissue, probe 100 is withdrawn from the body using bending and retraction until it is straightened and may be pulled back from the needle.

Other Surgical Probe Embodiments

In FIG. 13 is schematically illustrated an exemplary surgical probe 1300 including a cutting section 1306 having a rotary cutting blade 1310 with rotary cutting wheels 1326 forming an angle θ with a longitudinal axis of the probe, according to some embodiments of the present invention.

Figure 14:
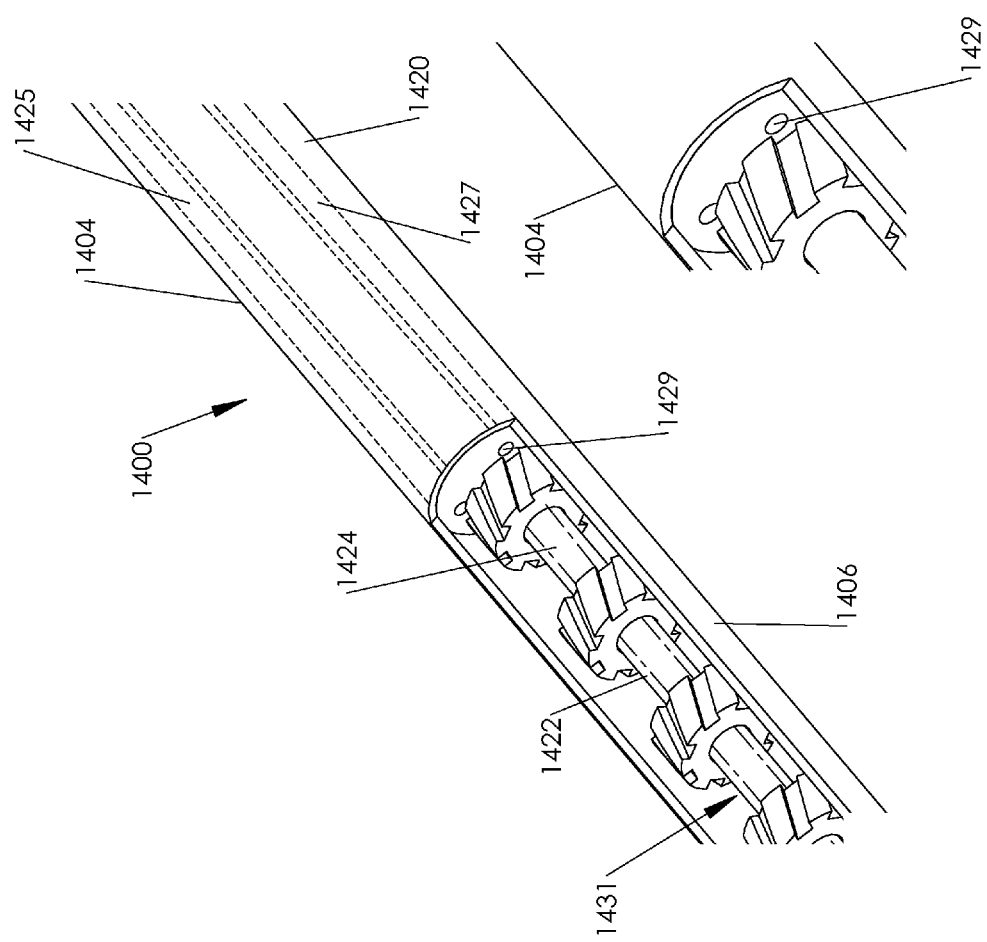
FIG. 14 schematically illustrates an exemplary surgical probe including a plurality of lumens (conduits) suitable for fluid conduction and/or aspiration, according to some embodiments of the present invention.

In FIG. 14 is schematically illustrated an exemplary surgical probe 1400 including a plurality of lumens (conduits) suitable for fluid conduction and/or aspiration, according to some embodiments of the present invention. Surgical probe 1400 includes an inner lumen 1420 in probe shaft 1404, a first lumen 1425 and second lumen 1427 inside the inner lumen, and a drive shaft conduit 1424 in drive shaft 1422. First and second lumens 1425 and 1427 include an opening 1429 at a distal end leading into a cavity 1431 in cutting section 1406 housing rotary cutting blade 1410. For example, a probe may include 1, 2, 3, 4, or a greater number of conduits.

Figure 15:
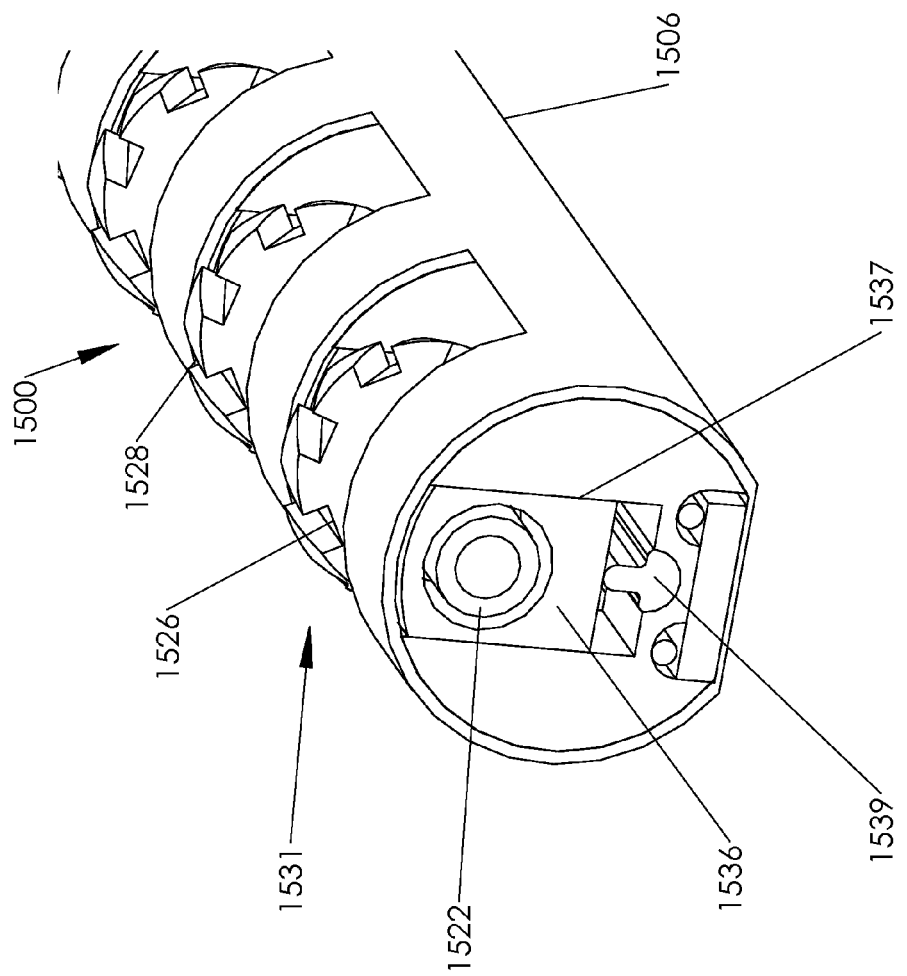
FIG. 15 schematically illustrates an exemplary surgical probe including a blade adjustment mechanism in a cutting section, according to some embodiments of the present invention.

In FIG. 15 is schematically illustrated an exemplary surgical probe 1500 including a blade adjustment mechanism 1531 in a cutting section 1506, according to some embodiments of the present invention. In an exemplary embodiment of the invention, blade adjustment mechanism 1531 adjusts a protrusion from cutting section 1506 of cutting edges 1528 in rotary cutting wheels 1526. Optionally, blade adjustment mechanism 1531 includes a pivotal cam mechanism 1539 adapted to act on a plurality of driving shaft supports 1536, raising and lowering the supports. Driving shaft supports 1536 support a flexible driving shaft 1522 which is maintained in alignment by a linear guide 1537 which aligns driving shaft supports 1536.

Figure 16A:
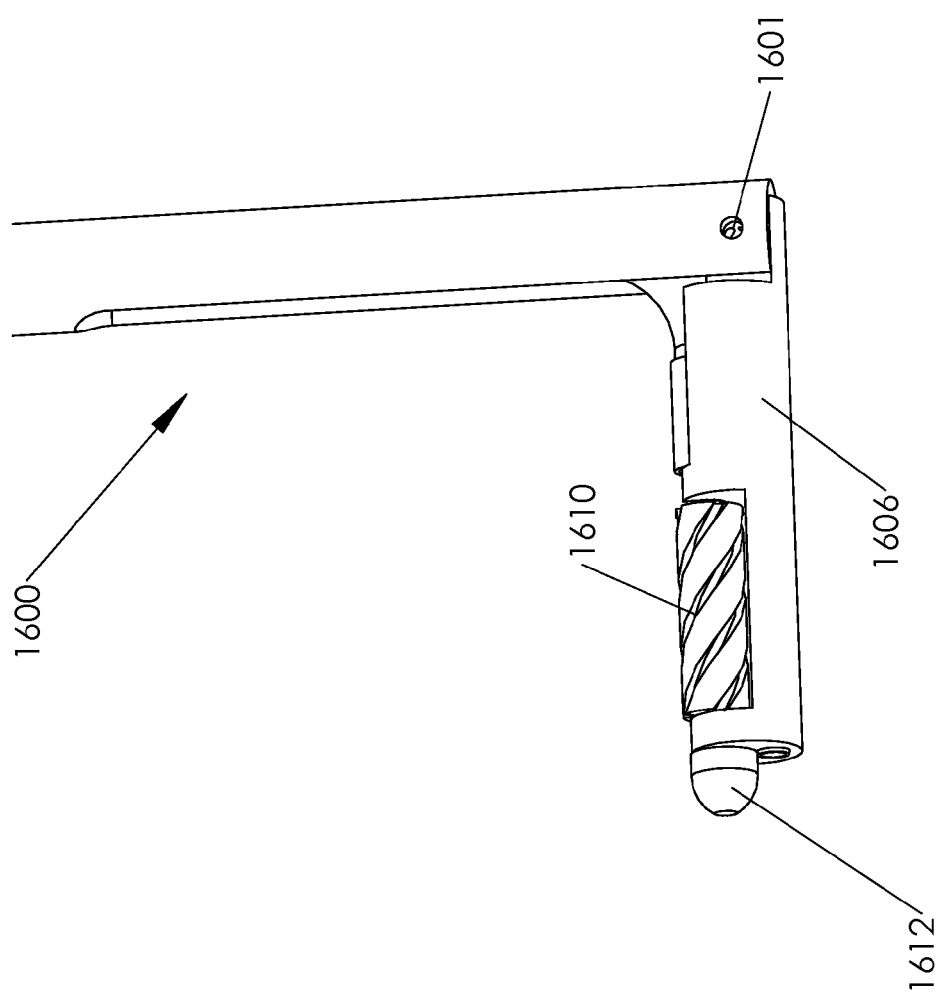
FIGS. 16A and 16B schematically illustrate an exemplary surgical probe including a distal section attached to an articulating joint and including frontal cutting tools, according to some embodiments of the present invention.
Figure 16B:
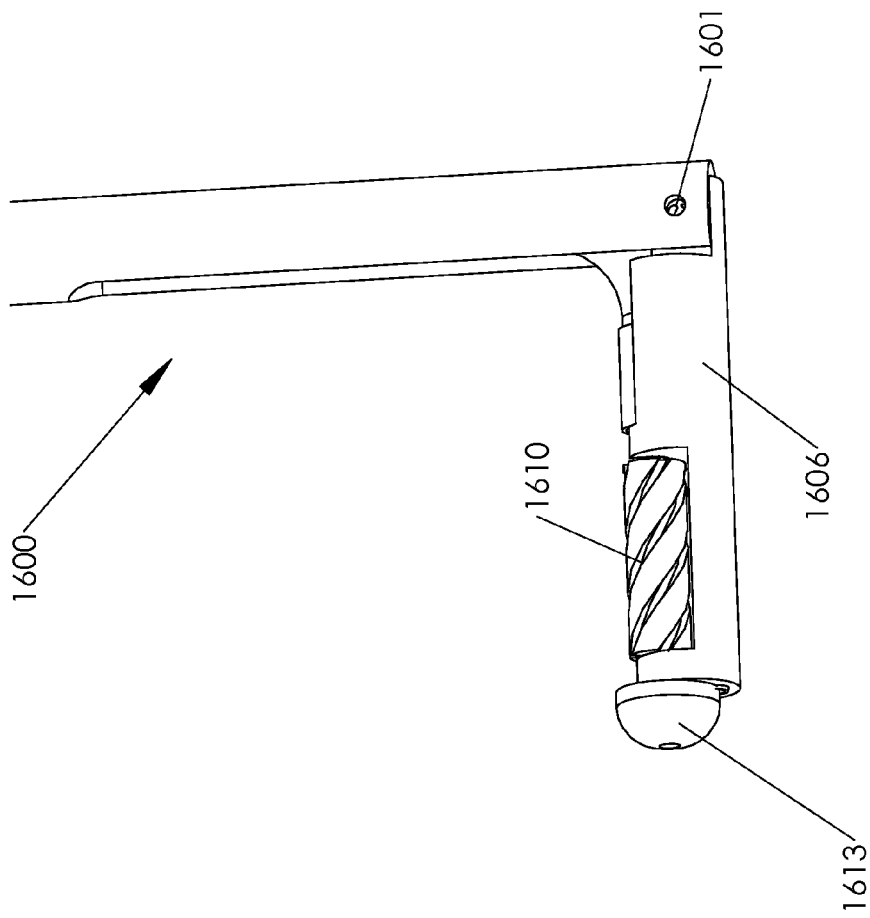

In FIGS. 16A and 16B are schematically illustrated an exemplary surgical probe 1600 including a distal section 1606 attached to an articulating joint 1601 (a hinge) and including frontal cutting tools 1612 and 1613, respectively, according to some embodiments of the present invention. Optionally, surgical probe 1600 includes a rotary cutting blade 1610 for lateral cutting. In FIG. 16A, surgical probe 1600 is shown with frontal cutting tool 1612 covering a portion of a cross-section of the tip at the distal end of the probe. In FIG. 16B, surgical probe 1600 is shown with frontal cutting tool 1612 covering the full cross-section of the tip at the distal end of the probe.

Figure 17A:
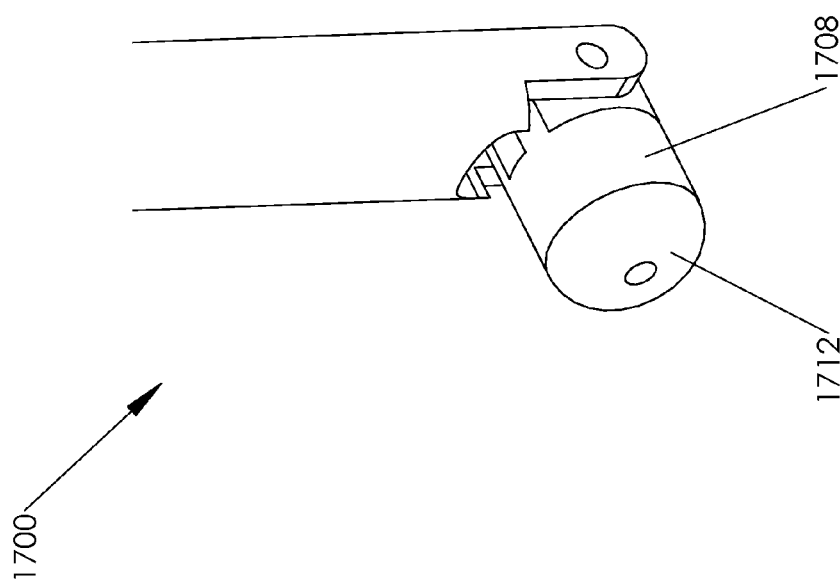
FIGS. 17A and 17B schematically illustrate perspective views of an exemplary probe including an articulating telescopic tip and a frontal cutting tool, according to some embodiments of the present invention.
Figure 17B:
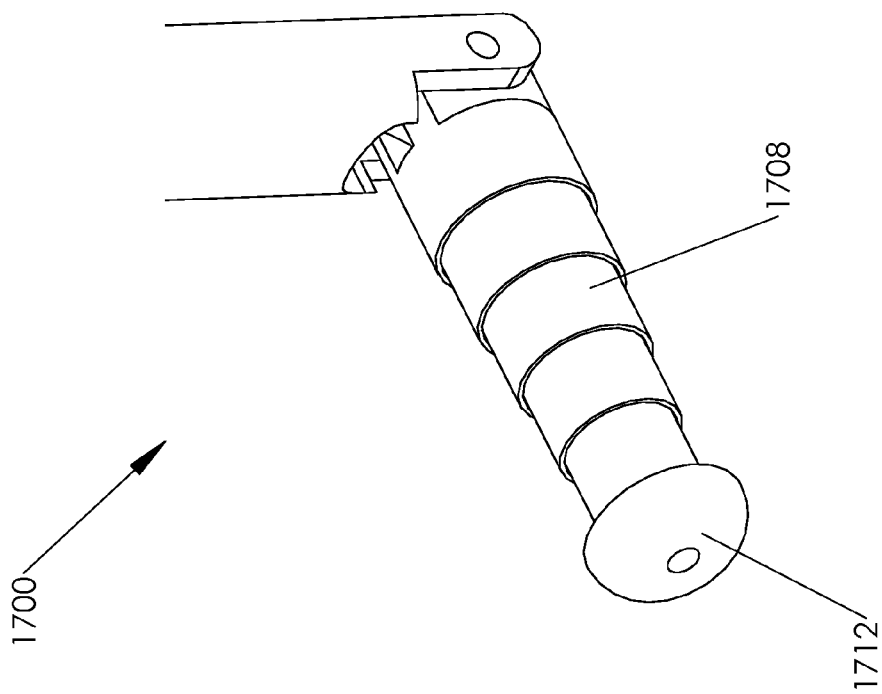

In FIGS. 17A and 17B are schematically illustrated perspective views of an exemplary probe including an articulating (hinged) telescopic tip 1708 and a frontal cutting tool 1712, according to some embodiments of the present invention. In FIG. 17A, tip 1708 is shown in a closed retracted position, while in FIG. 17B tip 1708 is shown in an open expanded position. In some embodiments, frontal cutting tool 1712 may be used when telescopic tip 1708 is partially opened. Optionally, opening and closing of telescopic tip 1708 is by means of a push wire (not shown).

Figure 18A:
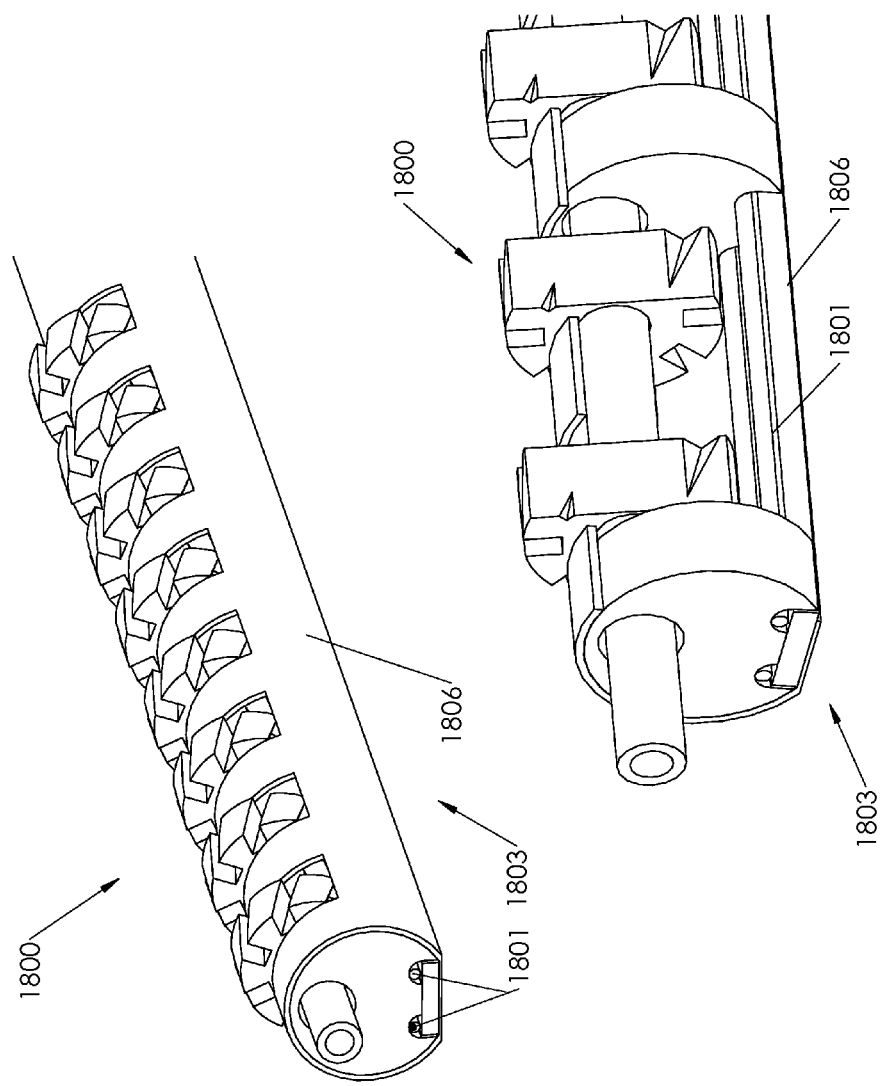
FIGS. 18A and 18B schematically illustrate an exemplary movement mechanism for bending a flexible cutting section in a surgical probe, according to some embodiments of the present invention.
Figure 18B:
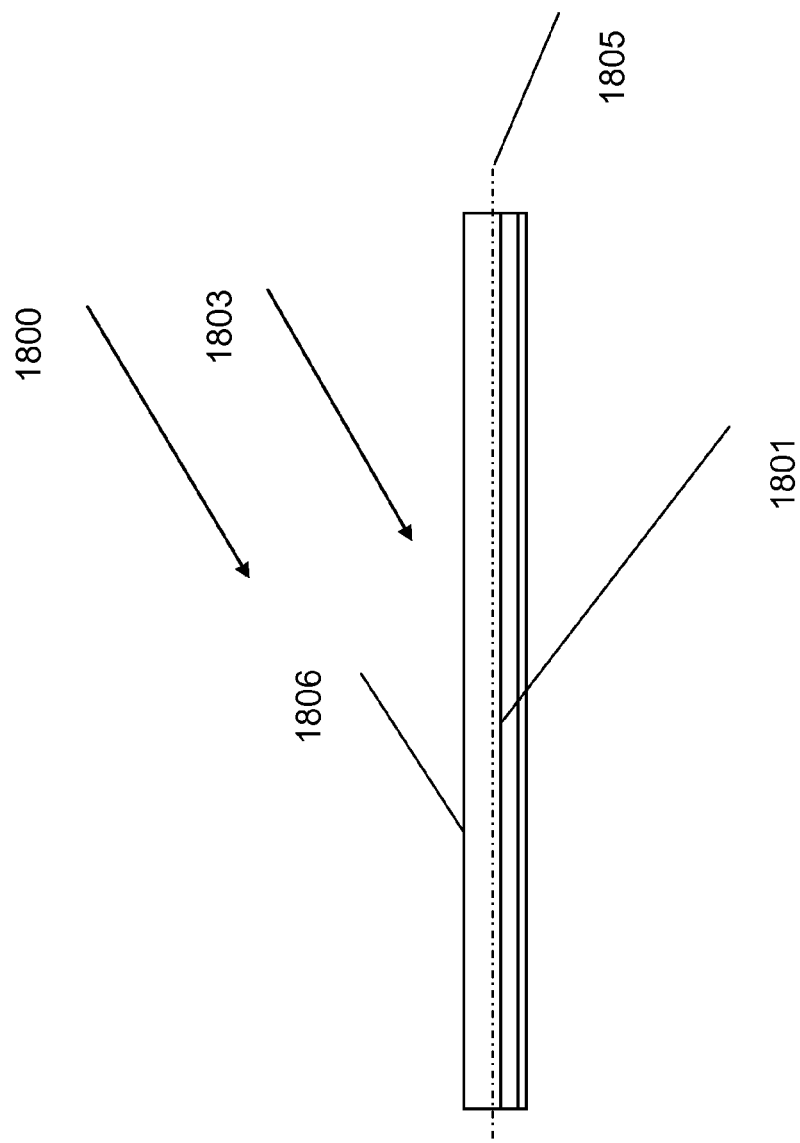

In FIGS. 18A and 18B are schematically illustrated an exemplary movement mechanism 1803 for bending a flexible cutting section 1806 in a surgical probe 1800, according to some embodiments of the present invention. Movement mechanism 1803 includes at least one pull wire 1801 positioned off-axis of a natural bending axis 1805 of cutting section 1806 and attached to a distal end of the cutting section. Pulling of pull wire 1801 will cause the side of cutting section 1806 where the wire is located to be shortened relative to the opposing side, bending the cutting section. Optionally, a pull wire may be included off-axis on each side of natural bending axis 1805 for allowing bending in opposing directions. For example, two or three or more such wires are provided. Optionally, at least one wire is attached at a different axial location from other wires, supporting more complex bending shapes.

In an exemplary embodiment of the invention, a conduit is used to pass a shaping stylet.

Figure 19:
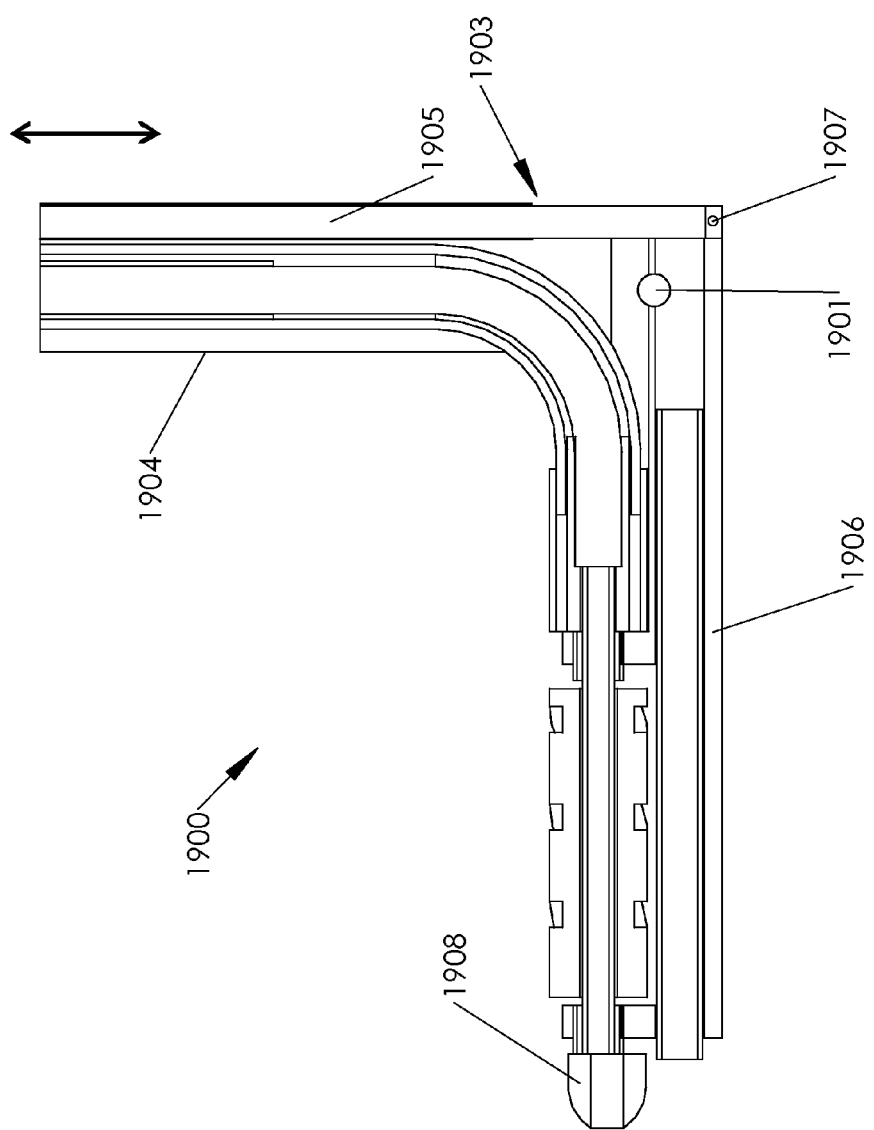
FIG. 19 schematically illustrates an exemplary movement mechanism for a surgical probe having an articulation joint, according to some embodiments of the present invention.

In FIG. 19 is schematically illustrated an exemplary movement mechanism for a surgical probe 1900 having an articulation joint 1901 (for example, a hinge), according to some embodiments of the present invention. Movement mechanism 1903 includes a push/pull rod 1905 which extends through probe shaft 1904 and connects to a hinge 1907 in cutting section 1906. Hinge 1907 is positioned such that pushing or pulling of rod 1905 will cause cutting section 1906 to rotate about hinge 1901 such that a distal tip 1908 will move in a direction opposite to that of rod 1905.

Other tool bending mechanisms, for example, those known in the art of endoscopes or trocars may be used.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

What is claimed is:

1. A surgical device for removing tissue from a body organ comprising:
an elongated shaft distally attached to a flexible cutting section having a plurality of rotary cutting edges, wherein said plurality of cutting edges are composed of a plurality of separate cutting discs, said flexible cutting section configured to be bent at at least one point between adjacent cutting edges; and
a user-operated controller proximally attached to said elongated shaft for selecting an angle of bending of said flexible cutting section at said at least one point.

2. The surgical device according to claim 1 wherein a distal section of said surgical device includes a shield for shielding tissue within the body organ from said cutting edges.

3. The surgical device according to claim 2 wherein said shield is rotatable around and/or axially movable along a longitudinal axis of said cutting section.

4. The surgical device according to claim 1 wherein said user-operated controller is further configured for adjusting a distance at least a portion of said cutting edges protrude transaxially from said cutting section.

5. The surgical device according to claim 4 wherein said user-operated controller is further configured to vary said protruding distance along a length of the cutting section.

6. The surgical device according to claim 4, further comprising blade adjustment mechanism including a rotary cam mechanism for adjusting the distance said at least a portion of said cutting edges protrude transaxially from said cutting section.

7. The surgical device according to claim 1, wherein said controller is further configured to control bending of said cutting section during cutting prior to advancing of said device within the body organ.

8. The surgical device according to claim 1 wherein said cutting section defines an elongate concave shape inside the body organ.

9. The surgical device according to claim 1 wherein said cutting section is configured to axially bend along an angle ranging from −270 degrees to +270 degrees in a single plane.

10. The surgical device according to claim 1 wherein said cutting section is configured to axially bend along an angle ranging from −270 degrees to +270 degrees in three dimensional space.

11. The surgical device according to claim 1 including a movement mechanism for bending said cutting section, wherein said movement mechanism includes at least one pull wire.

12. The surgical device according to claim 11 wherein said at least one pull wire is positioned so that it lays off-axis relative to a natural bending axis of said cutting section.

13. The surgical device according to claim 1 wherein said cutting section includes a frontal cutting tool.

14. The surgical device according to claim 13 wherein said frontal cutting tool is selected from a drill, a burr, a rasp, and a vibratory element.

15. The surgical device according to claim 1 wherein said at least one point is a predefined joint.

16. The surgical device according to claim 1, wherein said cutting section is bendable relative to said elongated shaft such that their longitudinal axes are at an angle in the range of from 30 to 150 degrees relative to one another.

17. The device according to claim 1, wherein said device includes at least two conduits reaching to a distal end of said elongated shaft, said at least two conduits configured to at least one of:
  deliver fluid to the body organ; and
  aspirate at least one of cut tissue and fluid from the body organ.

18. The device according to claim 1, wherein said flexible cutting section is configured to bend at a first portion into a concave shape and to bend at a second portion into a convex shape.

19. The device according to claim 1, wherein said flexible cutting section is configured to bend to substantially match a shape of a surface of a bone.

20. A surgical device for removing tissue material from under a tissue surface comprising an elongated shaft and a distally attached tip including a cutting tool having a plurality of rotary cutting blades, wherein said plurality of cutting blades are composed of a plurality of separate cutting discs, said distally attached tip attached to said elongated shaft such that their longitudinal axes are at least at an angle less than 150 degrees relative to one another.

21. The surgical device according to claim 20, wherein said device is configured to form a cavity under the tissue surface.

22. A method for removing tissue from a body organ comprising:
  inserting a cutting tool via a small opening and forward-cutting tissue from said organ using a rotary cutting action;
  advancing said forward-cutting using a rotary cutting action based on determining an amount of tissue removed by said forward-cutting, said advancing including selecting at least one of a bending angle and a bending point of said cutting tool, said cutting tool having a plurality of rotary cutting edges, wherein said plurality of cutting edges are composed of a plurality of separate cutting discs;
  simultaneously forward-cutting and laterally cutting tissue using said rotary cutting action; and
  advancing said forward- and lateral cutting based on determining an amount of tissue removed by said forward- and lateral cutting;
  wherein said selecting at least one of a bending angle and a bending point is controlled by a user-operated controller proximally positioned along a shaft.

23. The method according to claim 22, wherein said advancing is based on feedback.

24. The method according to claim 22, further comprising at least laterally expanding said cutting tool while maintaining a constant width of a distal portion of said device.

25. The method according to claim 24, wherein said selecting includes at least one of bending said tool and rotating said tool relative to a direction of said forward-cutting.

26. The method according to claim 25, wherein each of said advancing, said at least one of bending and rotating, and said cutting is performed independently.

27. The method according to claim 22, wherein said tissue removal forms an indirect passage.

28. The method according to claim 22, wherein said tissue removal is between a ligament in the spinal column and a spinal bone.

29. The method according to claim 22, further comprising cutting while a cutting section of a cutting tool is bent, prior to said advancing.

30. The method according to claim 22, further comprising controlling cutting parameters from outside the body by a user, said cutting parameters including said bending angle, a distance at least a cutting edge of said tool protrudes transaxially from a cutting section of said tool, and rotation of at least a portion of said tool.

* * * * *